(12) United States Patent
Mihalcioiu et al.

(10) Patent No.: US 9,057,055 B2
(45) Date of Patent: Jun. 16, 2015

(54) METHOD OF OBTAINING CIRCULATING CANCER CELL POPULATIONS

(71) Applicant: THE ROYAL INSTITUTION FOR THE ADVANCEMENT OF LEARNING/MCGILL UNIVERSITY, Montreal (CA)

(72) Inventors: Catalin Mihalcioiu, Montreal (CA); Richard Kremer, Westmount (CA); Michael Sebag, Montreal (CA); Ramy Saleh, Montreal (CA); Jiarong Li, Montreal (CA)

(73) Assignee: THE ROYAL INSTITUTION FOR THE ADVANCEMENT OF LEARNING/MCGILL UNIVERSITY, Montreal, QC (CA)

( * ) Notice: Subject to any disclaimer, the term of this patent is extended or adjusted under 35 U.S.C. 154(b) by 0 days.

(21) Appl. No.: 14/097,605

(22) Filed: Dec. 5, 2013

(65) Prior Publication Data

US 2014/0154799 A1 Jun. 5, 2014

Related U.S. Application Data

(60) Provisional application No. 61/733,537, filed on Dec. 5, 2012.

(51) Int. Cl.
*C12N 5/07* (2010.01)
*C12N 5/09* (2010.01)
*C12N 5/095* (2010.01)

(52) U.S. Cl.
CPC ............ *C12N 5/0694* (2013.01); *C12N 5/0695* (2013.01)

(58) Field of Classification Search
USPC ...................................... 435/344, 344.1, 372
See application file for complete search history.

(56) References Cited

U.S. PATENT DOCUMENTS

| 6,960,449 | B2 | 11/2005 | Wang et al. |
| 8,105,793 | B2 | 1/2012 | Connelly et al. |
| 8,123,713 | B2 | 2/2012 | Felt et al. |
| 2002/0098535 | A1 | 7/2002 | Wang et al. |
| 2011/0189670 | A1* | 8/2011 | Katz et al. .................... 435/6.11 |

OTHER PUBLICATIONS

Mostert B. et al. Circulating Tumor Cells. Cancer Treatment Reviews 35:463-474, 2009.*
Yu, M. et al. Circulating Tumor Cells. J Cell Biology 192(3)373-382, Feb. 2011.*
Mihalcioiu et al., Detection, enrichment, characterization and propagation of circulating tumour cells from patients with advanced metastatic breast cancer, Presented at the San Antonio Breast Cancer Symposium, held between Dec. 6 to 10, 2011 in San Antonio, Texas.

* cited by examiner

*Primary Examiner* — Ralph Gitomer
(74) *Attorney, Agent, or Firm* — Norton Rose Fulbright Canada LLP

(57) ABSTRACT

It is herewith provided methods of obtaining circulating cancer cells (CCCs)-enriched cellular populations based on the removal of CD45-positive cells from an apheresis product. It is also provided methods of obtaining circulating stem cells (CSCs)-enriched cellular population from a CCCs-enriched cellular population based on a selection either using the specific cellular markers or through culture. It is further provided methods of obtaining circulating tumor cells (CTCs)-enriched cellular population from a CCCs-enriched cellular population based on a selection using the specific cellular markers. It is also provided screening assays for the selection of (chemo)therapeutic agent as well as personalized medicine application based on drug sensitivity/resistance or cancer markers.

13 Claims, 9 Drawing Sheets

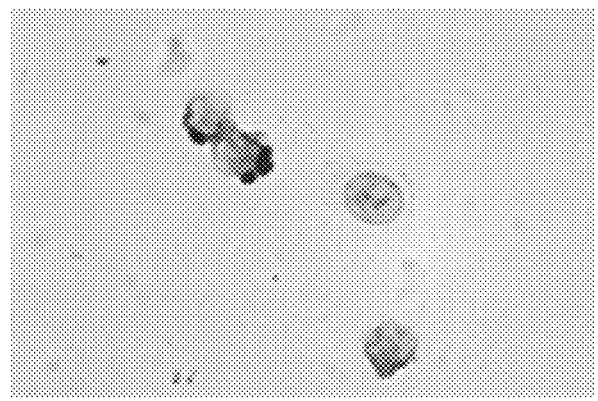
FIGURE 4
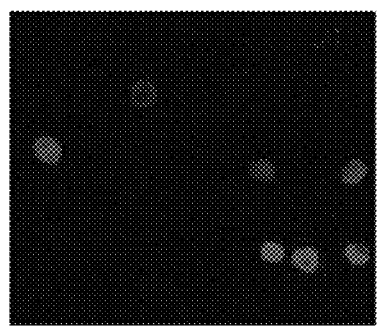   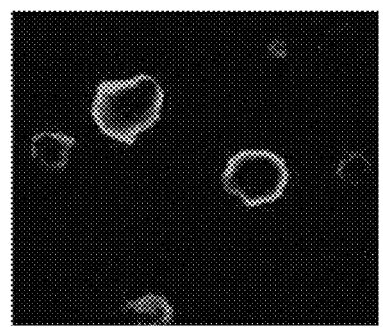
FIGURE 5a          FIGURE 5b
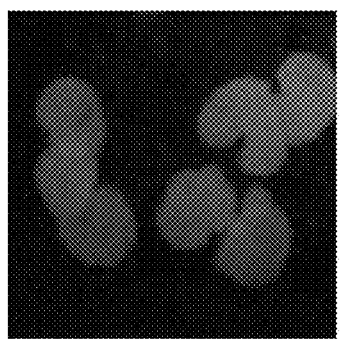   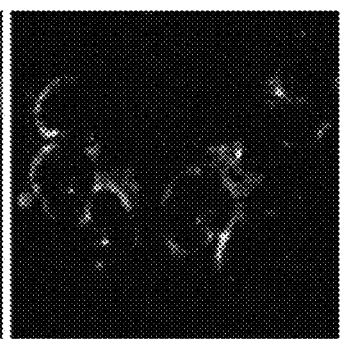   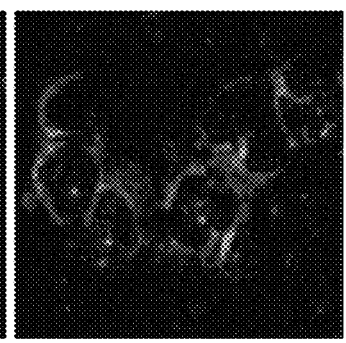
FIGURE 6a          FIGURE 6b          FIGURE 6c

FIGURE 9
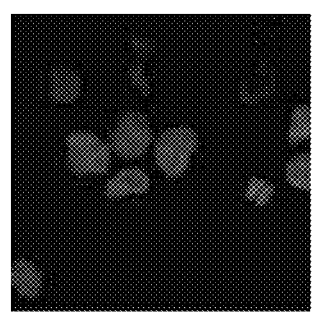 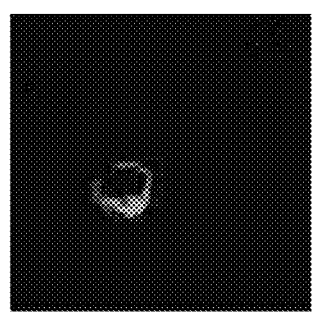 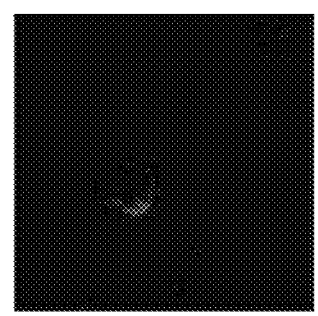
FIGURE 10a  FIGURE 10b  FIGURE 10c

FIGURE 12a
 
FIGURE 12b  FIGURE 12c

METHOD OF OBTAINING CIRCULATING CANCER CELL POPULATIONS

CROSS-REFERENCE TO RELATED APPLICATIONS

This application claims priority from U.S. provisional patent application Ser. No. 61/733,537 filed on Dec. 5, 2012 and herewith incorporated in its entirety.

TECHNOLOGICAL FIELD

This present disclosure relates to methods of obtaining circulating cancer cells (including circulating tumor cells, circulating stem cells and/or circulating epithelial-mesenchymal transition cells), isolated populations of circulating cancer cells as well as use of these cellular populations in screening assays for cancer therapeutic discovery and in predictive assays for personalized medicine.

BACKGROUND

Circulating tumors cells (CTCs) are shed from the primary tumor or its metastatic sites and recapitulate many of the features of tumor heterogeneity. Importantly, the CTCs number follow closely the progression or regression of the disease. However, CTCs circulate in very low number making it difficult to characterized them using standard blood test procedures.

There is no gold standard to refer to, as there is no optimal platform that has yet permitted detailed molecular and functional characterization of the CTCs. The most widely used methods are positive selection methods based on antigen capture on the surface of CTCs using antibodies bound to magnetic particles. They rely on the universal epithelial marker EpCAM (CD326) present on CTCs but absent from white blood cells. For example, the CellSearch™ (Veridex) method is FDA-approved and uses positive selection by anti-EpCAM antibodies followed by cytokeratin histological confirmation. Non-specific background of leukocytes is eliminated using a CD45 staining. However, this method suffers from several drawbacks, including low sensitivity of detection (less than 40% of patients with chemotherapy naïve advanced cancer are identified) as a minimum of 4 CTCs/mL of blood is necessary to positively identify patients. In addition, due to the destructive nature of the CellSearch™ method, it is not amenable to full isolation and molecular characterization of viable CTCs.

EpCAM antibodies have also been used alternatively to isolate or characterize CTCs. In another example, multiple chambers coated with anti-EpCAM antibodies are used to collect CTCs from peripheral blood. This technique is amenable to enumeration and analysis of around 50 CTCs/mL of blood (total of around 100 to 200 CTCs/chip using 2 to 4 mL of blood). This technology permitted longitudinal monitoring of patients. In a further example, characterization by flow cytometry has also been reported using few mL of collected peripheral blood but its applicability is limited by its sensitivity to detect the low number of cells present in a small blood sample. In still another example, the MagSweeper™ which is an alternate magnetic bead method coated with anti-EpCAM antibodies is another available platform to recuperate CTCs from peripheral blood.

Other approaches, not based on EpCAM expression, have also been used including nucleic acid detection methods and isolation methods based on physical characteristics of CTCs. The former approach based on detection of released DNA or RNA from CTCs lacks specificity and relies on PCR based detection of rare cells among large quantities of white blood cells resulting in many false negative or positive tests. On the other hand, detection and isolation of CTCs based on physical properties has potential value because of its relative simplicity, detection irrespective of cell surface markers, low cost and amenability to high throughput screening. However, such platforms relying on cell size and density are flawed by the inherent heterogeneity of CTCs, which vary widely in size within and between patients. Finally, a number of cell based scanning techniques are also emerging using fiber optic or laser scanning for cytological evaluation. However, these methods will also need further careful validation.

It would be highly desirable to be provided with a method of obtaining circulating tumor cells populations, preferably in a viable form, to allow the further characterization of these populations of cells. It would also be highly desirable to be provided with a method of obtaining other circulating cancer cells populations, preferably in a viable form, to allow the further characterization of these population of cells. These cellular populations could be used in screening assays to identify potential anti-cancer therapeutic agents. Alternatively or in combination, these cellular populations can also be used to provide personalized medicine services to cancer patients.

BRIEF SUMMARY

The present disclosure concerns process associated with the collection of circulating cancer cells comprising circulating stem cells and/or circulating tumor cells as well as methods associated thereto. These methods and processes are based on depletion of CD45-positive cells from an apheresis nucleated cellular product.

In a first aspect, there is provided a method of providing a population of cells enriched in circulating cancer cells. Broadly, the method comprises a) depleting an apheresis nucleated cellular product from CD45-positive leukocytes to provide the population of cells enriched in circulating cancer cells; and b) collecting the population of cells enriched in circulating cancer cells. In an embodiment, the method further comprises c) culturing the population of cells enriched in circulating cancer cells. In some embodiment, the method of further comprises culturing the population of cells enriched in circulating cancer cells in non-adherent conditions and/or under conditions allowing the formation of at least one mammosphere. In an embodiment, the at least one mammosphere comprises circulating stem cells and step c) further comprises collecting the at least one mammosphere to obtain a population enriched in circulating stem cells. In another embodiment, the method further comprising, prior to step b), selecting cytokeratin (CK)-positive cells from the population of cells enriched in circulating cancer cells. In such embodiment, the population of cells enriched in circulating cancer cells can be a population of cells enriched in circulating tumor cells and step b) can further comprises collecting the population of cells enriched in circulating tumor cells. In another embodiment, the method further comprises, prior to step b), selecting epithelial cellular adhesion molecule (EpCAM)-positive-positive cells from the population of cells enriched in circulating cancer cells to obtain a population of cells enriched in circulating tumor cells and step b) further comprises collecting the population of cells enriched in circulating tumor cells. In another embodiment, the method further comprises, prior to step b), selecting CD24-negative and CD44-positive cells from the population of cells enriched in circulating cancer cells to provide a population of cells enriched in circulating stem cells, and, at step b), collecting the population of cells enriched in circulating stem cells. In such embodiment, the method can further comprise, prior to step b) selecting aldehyde dehydrogenase isoform 1 (ALDH1)-positive cells and/or EpCAM-negative cells from the population of cells enriched in circulating cancer cells to provide the population of cells enriched in circulating stem cells. In another embodiment, the method further comprises, prior to step b), selecting CK-negative cells from the population of cells enriched in circulating cancer cells to obtain a population of cells enriched in circulating epithelial mesenchymal transition cells and, at step b), collecting the population of cells enriched in circulating epithelial mesenchymal transition cells. In such embodiment, the method can further comprise, prior to step b), selecting vimentin-positive cells, E-cadherin-negative and/or N-cadherin-positive cells from the population of cells enriched in circulating cancer cells to obtain the population of cells enriched in circulating epithelial mesenchymal transition cells. In an embodiment, the apheresis nucleated cellular product is from a subject having a cancer (for example, a melanoma or a carcinoma (e.g., a breast carcinoma, a colorectal carcinoma, a prostate carcinoma and/or a lung carcinoma).

According to a second aspect, there is provided a population of cells enriched in circulating cancer cells obtained by the method described herein.

According to a third aspect, there is provided a population of cells enriched in circulating stem cells obtained by the method described herein.

According to a fourth aspect, there is provided a population of cells enriched in circulating tumor cells obtained by the method described herein.

According to a fifth aspect, there is provided a population of cells enriched in circulating stem cells obtained by the method described herein.

According to a sixth aspect, there is provided a population of cells enriched in circulating epithelial mesenchymal transition cells obtained by the method described herein.

According to a seventh aspect, there is provided a method of providing a population of cells enriched in circulating cancer cells. Broadly, the method comprises a) depleting an apheresis nucleated cellular product from leukocytes to provide the population of cells enriched in circulating cancer cells; and b) collecting the population of cells enriched in circulating cancer cells. In an embodiment, the leukocytes are CD45-positive cells. In another embodiment, step a) further comprises removing CD45-positive cells from the apheresis nucleated cellular product (e.g. optionally with an anti-CD45 antibody). In another embodiment, the apheresis nucleated cellular product is enriched in nucleated cells and, in still a further embodiment, the method further comprises, prior to step a), submitting the apheresis nucleated cellular product to a density gradient. In still another embodiment, the method further comprises c) culturing the population of cells enriched in circulating cancer cells. In another embodiment, step c) comprises culturing the population of cells in non-adherent conditions, and in a further embodiment, step c) comprises the formation of at least one mammosphere. In still another embodiment, the population of cells enriched in circulating cancer cells comprises circulating tumor cells, such as, for example, viable circulating tumor cells. In another embodiment, the population of cell enriched in circulating cancer cells comprises circulating stem cells such as, for example, viable circulating stem cells. In some embodiment, the apheresis product is enriched in nucleated cells for example by, prior to step a), submitting the apheresis product to a density gradient. In some embodiments, the apheresis nucleated cellular product, prior to step a), comprises at least $3 \times 10^9$ total cells. In embodiments, the apheresis nucleated cellular product is from a subject having a cancer, such as, for example, a melanoma or a carcinoma (e.g., a breast carcinoma, a colorectal carcinoma, a prostate carcinoma or a lung carcinoma). In another embodiment, a population of cells enriched in circulating cancer cells obtained by the method described herein is also contemplated.

According to an eight aspect, there is provided method of providing a population of cells enriched in circulating stem cells. Broadly, the method comprises a) depleting an apheresis nucleated cellular product from leukocytes to obtain a first population of cells enriched in circulating cancer cells; b) selecting the circulating stem cells from the first population of cells to obtain a population of cells enriched in circulating stem cells; and c) collecting the population of cells enriched in circulating stem cells. In an embodiment, the leukocytes are CD45-positive cells. In another embodiment, step a) further comprises removing CD45-positive cells from the apheresis nucleated cellular product (e.g. optionally with an anti-CD45 antibody). In some embodiment, the circulating stem cells are CD24-negative and CD44-positive cells. In an embodiment, step b) further comprises selecting CD24-negative and CD44-positive cells (e.g. optionally with a combination of an anti-CD24 antibody and an anti-CD44 antibody). In some embodiments, the circulating stem cells are ALDH1-positive cells. In an embodiment, the method further comprises selecting ALDH1-positive cells (e.g. optionally with an anti-ALDH-1 antibody). In some embodiments, circulating stem cells are EpCAM-negative cells. In an embodiment, the method further comprises selecting EpCAM-negative cells (e.g. optionally with an anti-EpCAM antibody). In embodiments, step b) further comprises culturing the first population of cells. In such embodiment, the first population of cells is cultured in non-adherent conditions and/or until the formation of at least one mammosphere. In some embodiment, the apheresis product is enriched in nucleated cells for example by, prior to step a), submitting the apheresis product to a density gradient. In some embodiments, the apheresis nucleated cellular product, prior to step a), comprises at least $3 \times 10^9$ total cells. In embodiments, the population of cells enriched in circulating stem cells comprises viable circulating stem cells. In embodiments, the apheresis nucleated cellular product is from a subject having a cancer, such as, for example, a melanoma or a carcinoma (e.g., a breast carcinoma, a colorectal carcinoma, a prostate carcinoma or a lung carcinoma). In another embodiment, a population of cells enriched in circulating stem cells obtained by the method described herein is also contemplated.

According to a ninth aspect, there is provided a method of providing a population of cells enriched in circulating tumor cells. Broadly, the method comprises a) depleting an apheresis product from leukocytes to obtain a first population of cells enriched in circulating cancer cells; b) selecting circulating tumor cells from the first population of cells to obtain a population of cells enriched in circulating tumor cells; and c) collecting the population of cells enriched in circulating tumor cells. In an embodiment, the leukocytes are CD45-positive cells. In another embodiment, step a) further comprises removing CD45-positive cells from the apheresis nucleated cellular product (e.g. optionally with an anti-CD45 antibody). In an embodiment, the circulating tumor cells are epithelial cellular adhesion molecule (EpCAM)-positive cells. In such embodiment, step b) further comprises selecting EpCAM-positive cells (e.g. optionally with an anti-EpCAM antibody). In some embodiment, the apheresis product is enriched in nucleated cells for example by, prior to step a), submitting the apheresis product to a density gradient. In some embodiments, the apheresis nucleated cellular product, prior to step a), comprises at least $3\times10^9$ total cells. In embodiments, the population of cells enriched in circulating tumor cells comprises viable circulating tumor cells. In embodiments, the apheresis nucleated cellular product is from a subject having a cancer, such as, for example, a melanoma or a carcinoma (e.g., a breast carcinoma, a colorectal carcinoma, a prostate carcinoma or a lung carcinoma). In another embodiment, a population of cells enriched in circulating tumor cells obtained by the method described herein is also contemplated.

According to a tenth aspect, there is provided a screening method for determining the usefulness of an agent to prevent, treat and/or alleviate the symptoms of a cancer in a subject. Broadly, the method comprises a) combining a population of cells with the agent, wherein the population of cells is the population of cells enriched in circulating cancer cells described herein, the population of cells enriched in circulating stem cells described herein and/or the population of cells enriched in circulating tumor cells described herein; b) obtaining a test value of at least one parameter of the population of cells in the presence of the agent; c) comparing the test value to a control value of the at least one parameter, wherein the control value is associated with the cancer or a lack of ability to prevent, treat and/or alleviate the symptoms of the cancer; and d) characterizing the agent based on the comparison. In an embodiment, the at least one parameter is the number of cells of the population of cells and step d) further comprises characterizing the agent (i) as useful for the prevention, treatment and/or alleviation of symptoms of the cancer if the test value is lower than the control value (ii) or as lacking usefulness for the prevention, treatment and/or alleviation of symptoms if the test value is equal to or higher than the control value. In another embodiment, the at least one parameter is the proliferation rate of the cells of the population of cells and step d) further comprises characterizing the agent (i) as useful for the prevention, treatment and/or alleviation of symptoms of the cancer if the test value is lower than the control value (ii) or as lacking usefulness for the prevention, treatment and/or alleviation of symptoms if the test value is equal to or higher than the control value. In still another embodiment, the at least one parameter is the viability of the cells of the population of cells and step d) further comprises characterizing the agent (i) as useful for the prevention, treatment and/or alleviation of symptoms of the cancer if the test value is associated with a lower viability than the control value (ii) or as lacking usefulness for the prevention, treatment and/or alleviation of symptoms if the test value is associated with a similar or higher viability than the control value. In an embodiment, the population of cells is the population of cells enriched in circulating stem cells described herein and the cancer is a metastatic cancer. In an embodiment, the cancer is a melanoma or a carcinoma (e.g. a breast carcinoma, a colorectal carcinoma, a prostate carcinoma or a lung carcinoma).

According to an eleventh aspect, there is provided a method of determining the sensitivity of a cancer subject to a therapeutic agent. Broadly the method comprises a) combining a population of cells obtained from the subject with the therapeutic agent, wherein the population of cells is the population of cells enriched in circulating cancer cells described herein, the population of cells enriched in circulating stem cells described herein and/or the population of cells enriched in circulating tumor cells described herein; b) obtaining a test value of at least one parameter of the population of cells in the presence of the agent; c) comparing the test value to a control value of the at least one parameter, wherein the control value is associated with a lack of sensitivity of cancer cells for the therapeutic agent; and d) determining the sensitivity of the population of cells for the therapeutic agent based on the comparison. In an embodiment, the at least one parameter is the number of cells of the population of cells and step d) further comprises characterizing the subject (i) as being sensitive to the therapeutic agent if the test value is lower number than the control value (ii) or as lacking sensitivity to the therapeutic agent if the test value is equal to or higher than the control value. In another embodiment, the at least one parameter is the proliferation rate of the cells of the population of cells and step d) further comprises characterizing the subject (i) as being sensitive to the therapeutic agent if the test value is lower than the control value (ii) or as lacking sensitivity to the therapeutic agent if the test value is equal to or higher than the control value. In still another embodiment, the at least one parameter is the viability of the cells of the population of cells and step d) further comprises characterizing the subject (i) as being sensitive to the therapeutic agent if the test value is associated with a lower viability than the control value (ii) or as lacking sensitivity to the therapeutic agent if the test value is associated with a similar or higher viability than the control value. In some embodiment, the method further comprises administering the therapeutic agent if the subject is characterized as being sensitive to the therapeutic agent. In an embodiment, the cancer is a melanoma or a carcinoma (e.g. a breast carcinoma, a colorectal carcinoma, a prostate carcinoma or a lung carcinoma).

According to a twelfth aspect, there is provided a method of characterizing the cancer status in a subject. Broadly, the method comprises a) providing a first test value of at least one cancer marker of a first population of cells obtained from the subject, wherein the first population of cells is the population of cells enriched in circulating cancer cells described herein, the population of cells enriched in circulating stem cells described herein and/or the population of cells enriched in circulating tumor cells described herein; and b) determining the cancer status based on the test value. In some embodiment, the method further comprises c) providing a second test value of the at least one cancer marker of a second population of cells obtained from the subject at a later point in time, wherein the second population of cells is the population of cells enriched in circulating cancer cells described herein, the population of cells enriched in circulating stem cells described herein and/or the population of cells enriched in circulating tumor cells described herein; d) comparing the first test value to the second test value; and e) characterizing the cancer status based on the comparison. In such embodiment, the first population of cells can be obtained from the subject before the administration of a first dose of a therapeutic agent and the second population of cells can be obtained from the subject after the administration of the first dose. Alternatively, the first population of cells can be obtained from the subject before the administration of a subsequent dose of a therapeutic agent and the second population of cells can be obtained from the subject after the administration of the subsequent dose. In some embodiment, the method further comprises c) providing a second test value of the at least one cancer marker of a primary tumor and/or a metastasis of the subject; d) comparing the first test value to the second test value; and e) characterizing the cancer status based on the comparison. In embodiments, the cancer status is a cancer subclass, a predisposition to form a metastasis, a predisposition to form a metastasis at a specific site and/or a sensitivity or a resistance to a therapeutic agent. In an embodiment, the cancer is a melanoma or a carcinoma (e.g. a breast carcinoma, a colorectal carcinoma, a prostate carcinoma or a lung carcinoma).

BRIEF DESCRIPTION OF THE DRAWINGS

Having thus generally described the nature of the invention, reference will now be made to the accompanying drawings, showing by way of illustration, a preferred embodiment thereof, and in which:

FIG. 4 shows a representative immunostaining of ANCP-enriched CCCs grown in a MammoCult™ media using an anti-E-cadherin antibody and visualized with an horseradish peroxidase/amino ethylcarbazole secondary antibody.

FIG. 5 shows a representative immunofluorescence of ANCP-enriched CCCs using (A) DAPI and (B) an anti-CXCR4 antibody. These results indicate that the non-cultured CCCs comprise CXCR4-positive nucleated cells. Such CXCR4 expression was also detected in cultured mammosphere CTC cells (15-day culture and subcultured three times, data not shown).

FIG. 6 shows a representative immunofluorescence of ANCP-enriched CCCs using (A) DAPI, (B) an anti-CK8 antibody and (C) an anti-CXCR4 antibody. These results indicate that the CCCs comprise CK8-positive/CXCR4-positive nucleated cells.

FIG. 9 shows a representative immunostaining using an anti-pan-cytokeratin antibody of a clump of cells present in the ANCP-derived fresh (e.g. non-cultured) CCCs from a breast cancer patient.

FIG. 10 shows a representative immunofluorescence mammospheres of ANCP-enriched CCCs cultured 15 days and subcultured three times. (A) DAPI, (B) anti-ERα antibody and (C) anti-CK8 antibody. These results indicate that, in this particular culture, one out of five cells is a CK8-positive/ERα-positive nucleated cells.

DETAILED DESCRIPTION

Figures 1A, 1B:
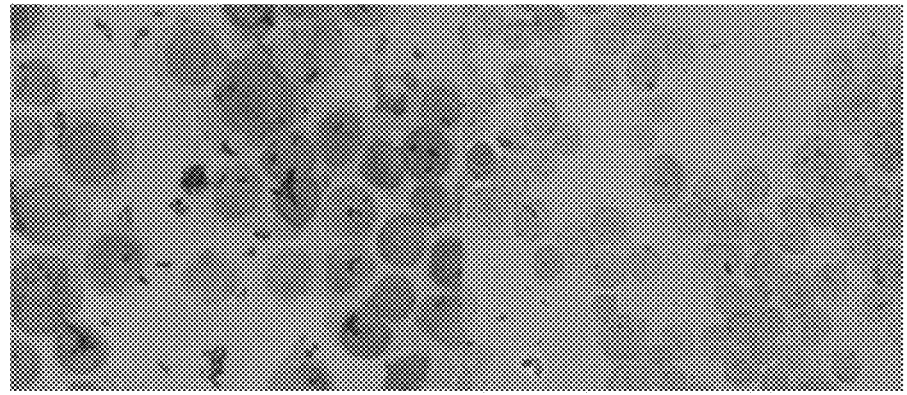
FIG. 1 shows representative immunostainings of cells using an anti-pan-cytokeratin monoclonal antibody A45-B/B3 and an alkaline phosphatase secondary antibody. (A) Peripheral blood-derived cells from a normal subject spike with MCF-7 cells, (B) control MCF7 cells which have not been incubated with the primary antibody, (C) and (D) representative ANCP-enriched fresh CCCs (cell clumps) from breast cancer patients.

Circulating tumor cells or CTCs are a population of cancer cells detected in the circulation of cancer patients. These cells have presumed important biological properties as their presence correlates with the metastatic process. In the art, they are defined as EpCAM/cytokeratin-positive and CD45-negative. The exact cellular composition of CTCs is unknown but it is now established that they represent a very heterogeneous population. Indeed, a small fraction of CTCs, probably less than 10%, harbors a more primitive, less differentiated phenotype, known as cancer stem cells (CSCs) that are EpCAM/cytokeratin-negative and CD45-negative, which are capable of reciprocal transformation (plasticity) into another cellular population known as epithelial mesenchymal transition cells (EMTCs). It is thought that this CSCs/EMTCs population is resistant to most current systemic therapies and can possibly re-emerge following the eradication of the primary tumor. CTCs circulate in low number and are difficult to isolate and characterize. Isolation of CSCs/EMT is even more challenging because of their even smaller number.

The present disclosure provides methods of obtaining circulating cancer cells (CCCs)-enriched cellular populations based on the removal of CD45-positive cells from an apheresis cellular product. The present disclosure also provides methods of obtaining circulating stem cells (CSCs)-enriched cellular population from a CCCs-enriched cellular population based on a selection either using the specific cellular markers or through culture. The present disclosure further provides methods of obtaining circulating tumor cells (CTCs)-enriched cellular population from a CCCs-enriched cellular population based on a selection using the specific cellular markers. The present disclosure also provides screening assays for the selection of (chemo)therapeutic agent as well as personalized medicine application based on drug sensitivity/resistance or cancer markers.

DEFINITIONS

Throughout this application, various terms are used and some of them are more precisely defined herein.

Apheresis nucleated cellular product (ANCP). As used herein, the terms "apheresis nucleated cellular product" and "ANCP" collectively refer to a cellular population of nucleated cells obtained by apheresis from the blood of a subject (e.g. in preferred embodiments, from the whole blood of the subject). The ANCP is not limited to a particular apheresis technique and as such can be obtained from continuous flow centrifugation (CFC) or intermittent flow centrifugation. Optionally, the ANCP can be submitted to a density gradient (for example a Ficoll™ gradient) to stratify cells (e.g., nucleated vs. anucleated cells) prior to its usage in the current methods. The apheresis nucleated cellular product preferably comprises nucleated and viable cells. In the art, the terms "apheresis" and "aphaeresis" are used interchangeably.

Cell clump. As used herein, the term cell clump (also referred to as a cellular clump or a clump of cells) refers to physically-associated CCCs. A cell clump comprises at least two CCCs, but it can also comprise up to ten CCCs. The CCCs of the cell clump can comprises CTCs, CSCs or a combination of CTCs and CSCs.

Circulating cancer cells (CCCs). As used herein, the terms "circulating cancer cells" and "CCCs" collectively refer to a cellular population comprising both circulating tumor cells and circulating stem cells. CCCs can be obtained from an apheresis product by conducting a negative selection for (e.g., the removal of) CD45-positive cells.

Circulating tumor cells (CTCs). As used herein, the term "circulating tumor cells" "CTCs" collectively refer to cells which, prior to culture, are CD45(−), CK(+) (e.g., CK8(+)), EpCAM(+) or (−) and are nucleated (e.g., DAPI (+)). CTCs are preferably obtained from ANCP of cancer patients (e.g. preferably afflicted by a melanoma or a carcinoma (breast, colorectal, lung or prostate)). In some embodiments, the presence of CTCs in the peripheral blood of cancer patients has been shown to correlate with the metastatic process (skeletal metastasis for example). However, their baseline level does not seem to be unrelated to tumor size.

Circulating Stem Cells (CSCs). As used herein, the term "circulating stem cells" or "CSCs" collectively refer to the combined population of tumor initiating cells/progenitor-like cells (e.g. cells which, prior to culture, are CD45(−), optionally CK(+) (e.g., CK8(+)), CD24(−), CD44(+) and are nucleated (e.g., DAPI (+)) and epithelial mesenchymal transition cells or EMTCs (e.g., cells which, prior to culture, are CD45 (−), CK(−) (e.g., CK8(−)), vimentin(+), and N-cadherin(+) and are nucleated (e.g., DAPI (+)). In some embodiments, circulating stem cells are EpCAM(−), even though some CSCs have been shown to be EpCAM(+). EMTCs have been described of being capable of epithelial mesenchymal transition, a process in which epithelial cells lose cell-to-cell adhesion through down-regulation of epithelial E-cadherin and up-regulation of mesenchymal N-cadherin thereby promoting invasion through the extracellular matrix as well as their release to metastatic targets. CSCs are preferably obtained from ANCP of cancer patients (e.g. preferably afflicted by a melanoma or a carcinoma (breast, colorectal, lung or prostate)).

Leukocytes. As used herein, the term leukocytes (also referred to as white blood cells or leucocytes) are cells of the immune system, derived from hematopoietic stem cells and involved in the immune response. Leukocytes include neutrophils, eosiniphils, basophils, lymphocytes and monocytes. In some embodiments, leukocytes express on their surface the CD45 marker.

Mammosphere. As used herein, the term mammosphere refers to cluster/agreggate of cancer cells grown in non-adherent conditions. In some embodiment, the use of a specific culture medium (such as the MammoCult™ media) can facilitate the formation of such mammosphere. The cell cluster is thought to arise from a single cell through clonal growth.

Prevention, treatment and alleviation of symptoms. These expressions refer to the ability of a method or an agent to limit the development, progression and/or symptomology of a cancer (e.g. preferably a melanoma or a carcinoma). Broadly, the prevention, treatment and/or alleviation of symptoms can encompass the reduction of proliferation of the cancer cells (e.g., by reducing the total number of cancer cells and/or by reducing the pace of proliferation of the cancer cells). In addition, the prevention, treatment and/or alleviation of symptoms can also encompass the reduction in primary tumor size as the reduction in the size and/or number of metastatic tumors. Symptoms associated with proliferation-associated disorder such as cancer include, but are not limited to: local symptoms which are associated with the site of the primary cancer (such as lumps or swelling (tumor), hemorrhage, ulceration and pain), metastatic symptoms which are associated to the spread of cancer to other locations in the body (such as enlarged lymph nodes, hepatomegaly, splenomegaly, pain, fracture of affected bones, and neurological symptoms), and systemic symptoms (such as weight loss, fatigue, excessive sweating, anemia and paraneoplastic phenomena).

Viability. As used herein, the term "viability" is intended to mean the capacity of a cell to perform its intended functions. The cell's functions may vary according to the type of cell. Cellular functions may include, for example, cellular division, translation, transcription, protein assembly and maturation, protein secretion, storage of compounds (e.g. proteins, lipids, etc.), responsiveness to external stimuli, migration, etc. A method wherein a cellular population remains "substantially viable" is one that does not irreversibly alter the cells' ability to perform its intended function (for example divide and replicate). For example, the method does not substantially induce cell death (either by apoptosis or necrosis) in a majority of cells.

Circulating Cancer Cells-Enrichment Process from Apheresis Nucleated Cellular Blood Product The present disclosure provides a novel approach to collect CCCs (CTCs and CSCs/EMT populations) using a procedure called apheresis. Broadly, the method comprises obtaining an apheresis nucleated cellular product (comprising nucleated cells) and removing the leukocytes from such apheresis nucleated cellular product. The cellular population obtain from this method is enriched in CCCs. Such cellular population can be divided into specific subpopulations (e.g. CTCs and CSCs) depending on the intended use.

In some embodiments, the methods described herein allow the recuperation of a population of CCCs that is more representative of the cancer state of the patient than other method relying on an EpCAM-positive selection prior to a CD45-negative selection. For example, some of the CCCs populations described herein comprise cell aggregates (or cellular clumps) which are believed to be associated with certain characteristics of the patient's cancer state. Methods relying on an EpCAM-positive selection prior to a CD45-negative selection have failed to identify such cellular aggregates. In another example, some of the CCCs described herein can be enriched to have circulating stem cells which are believed to be associated with the patient's cancer state. Methods relying on EpCAM-positive selection prior to a CD45-negative selection have failed to identify such circulating stem cells.

In the methods described herein, the various cellular populations are obtained from the apheresis of the blood of a cancer patient. In some embodiment, to recuperate an adequate amount of cells, the apheresis is conducted on the whole blood volume of the patient. In some embodiments, to recuperate an adequate amount of cells, the apheresis is conducted on at least 3 L of the patient's blood and, in alternate embodiment; the apheresis is conducted on at least 4 L of the patient's blood. In an alternative embodiment, to recuperate an adequate amount of cells, apheresis is conducted twice on the whole blood of the patient. The apheresis (also referred to as leukapheresis) process provides a blood fraction containing nucleated cells (such as for example, peripheral blood mononuclear cells (lymphocytes, monocytes and macrophages), basophils and eosinophils. In the context of the present disclosure, the apheresis generates an apheresis nucleated cellular product (also referred to as an ANCP) which contains CCCs. In one embodiment, prior to the enrichment methods described herein, the apheresis nucleated cellular product can be submitted to a density gradient (such as a Ficoll™ gradient) to separate cells into different compartments and to remove impurities (non-nucleated cells, cellular debris, etc.).

The ACNP used in the methods described herein are obtained from cancer patients. CCCs have been shown to be present in the peripheral blood of melanoma as well as carcinoma patients (for example, in breast carcinoma, colorectal carcinoma, gastrointestinal carcinoma, prostate carcinoma or lung carcinoma patients). Therefore, the methods described herein are particularly suited for obtaining CCCs-enriched populations from these patients.

Once obtained, the apheresis nucleated cellular product is submitted to a first negative selection step to remove leukocytes from the ANCP. This negative selection step is performed prior to any other selection step. This negative selection step is also performed prior to any in vitro culture. An advantageous way of conducting such first negative selection step is to remove CD45-positive cells from the ANCP. CD45 is a type I transmembrane protein that is usually expressed on all differentiated hematopoietic cells (except erythrocytes and plasma cells). CD45 is also expressed in lymphomas, B-cell chronic lymphocytic leukemia, hairy cell leukemia and acute non lymphocytic leukemia. More importantly, CD45 is not expressed on the surface of CCCs and as such can be used to successfully enriched the ANCP in CCCs. This negative selection step can conducted using an anti-CD45 antibody (or fragment thereof). In one embodiment, the CD45-positive cells are removed from the ANCP using a fluorescent anti-CD45 antibody and fluorescent-activated cell sorting. In an another embodiment, an immunoadsorbed anti-CD45 antibody can also be used. For example, the anti-CD45 antibody can be coupled to removal means. Such removal means can be a solid surface. In such embodiment, the CD45-positive cells will be trapped on the surface and the CCCs can be collected (as they will not be associated to the surface via the anti-CD45 antibody). In another embodiment, the removal means can be a bead (such as a magnetic bead) which will trap the CD45-positive cells. In such embodiment, the beads can be removed from the ANCP to provide the CCCs population. In an embodiment, this first negative selection removes at least 80%, at least 85%, at least 90%, at least 95% or at least 99% of the CD45-positive cells from the initial ANCP.

As indicated above, the population of freshly isolated (e.g. non-cultured) CCCs is an heterogeneous one and is specific for each cancer patient at a specific point in time. It is believed that the composition of the population of CCCs will be modulated during cancer progression, remission and even treatment. In some embodiments, the population of freshly isolated CCCs comprises CTCs (for example viable CTCs), CSCs (for example viable CSCs) as well as combinations thereof. In other embodiments, the population of freshly isolated CCCs comprises cellular aggregates. In some embodiments, the fresh CCCs obtained can also contain CD45-positive cells which have not been removed by the negative selection step above.

In some instances, it may be required to culture the population of CCCs obtained. This culture step may be warranted if the number of cells needs to be expanded (to provide, for example, an appropriate amount of cells for subsequent analysis steps). Such culture step may be performed in adherent as well as non-adherent conditions. In some embodiments, the population of cultured CCCs comprises CTCs (for example viable CTCs), CSCs (for example viable CSCs) as well as combinations thereof. In some embodiments, the populations of cultured CCCs comprise CSCs but not CTCs.

Once a population of CCCs is obtained, it can be optionally manipulated to provide another cellular population: a population enriched in CSCs. One of the advantages of the present method is that they allow the collection (isolation or purification) of viable CSCs. As indicated above for populations enriched in CCCs, it is believed that the composition of the population of CSCs will be modulated during cancer progression, remission and even treatment. In order to obtain a cellular population enriched in CSCs, various techniques can be used. In one embodiment, it is possible to preferably enrich a cellular population in CSCs using FACS or an immunoadsorption technique for surface markers associated to CSCs prior to any in vitro culture. In order to obtain a population enriched in CSCs, the population enriched in CCCs is submitted to a negative selection for CD24-positive cells (e.g. removal of CD24-positive cells from the population of CCCs) and to a positive selection for CD44-positive cells (e.g. selection of CD44-positive cells from the populations of CCCs) as well as a positive selection for CK-positive cells (e.g., selection of CK-positive cells (and in an embodiment, of CK8-positive cells) from the population of CCCs). These positive and negative selections can be made using FACS or immunoadsorption for example. In addition, the order in which the negative and selective selections occurs is irrelevant to obtain the population enriched in CSCs. The population of CSCs can be further divided upon the presence or absence of additional markers such as ALDH1, CD133 and EpCAM. Some CSCs subpopulations are ALDH1-positive (and can be obtained by conducting a positive ALDH1 selection), others are CD133-positive (and can be obtained by conducting a positive CD133 selection), whereas others are EpCAM-negative (and can be obtained by conducting a negative EpCAM selection).

In another embodiment (alternatively or in combination to selection), it is also possible to enrich the initial population of CCCs in CSCs by culturing the CCCs in non-adherent conditions (for example in ultra-low attachment culture vessel). In such conditions, mammospheres enriched in expanding CSCs can form and can be preferentially selected to obtain the population enriched in CSCs. For example, CCCs can be plated (at an initial density of from 20 to 30 up to 3.5 to $4 \times 10^4$ in 2 mL of culture media per well of a 6-well dish) and cultured until they form mammospheres. When the mammospheres reach approximately 60 µm in diameter, they can be sub-cultured (e.g. passed) by collecting, centrifuging and trypsinizing the cells. Such sub-culture (or passage) can be repeated 2, 4 or even 6 times. This non-adherent culture step is not limited to any particular culture media. However, a MammoCult™ media has been shown useful to allow the culture and expansion of CSCs as well as the formation of mammospheres. Using these conditions, and as shown herein, it is possible to expand 500- to 1 000-fold the initial number of CSCs.

The population enriched in CSCs can also be obtained by conducting marker selection (CK(+), CD24(−) and CD44(+)

selections) and then culturing the cellular populations obtained (e.g. forming mammospheres).

The population of CCCs is obtained can also be optionally manipulated to provide another cellular population: a population enriched in CTCs. As indicated above for the population enriched in CCCs, it is believed that the composition of the population of CTCs will be modulated during cancer progression, remission and even treatment. One of the advantages of the present method is that they allow the collection (isolation or purification) of viable CTCs.

Once the initial population enriched in CCCs is obtained, it can be submitted to a positive selection step to concentrate the CTCs. This positive selection step is based on the preferential expression of the epithelial cell adhesion molecule (EpCAM) and/or cytokeratin (such as cytokeratin 8 or CK8) on CTCs. As indicated above for populations enriched in CCCs, it is believed that the composition of the population of CTCs will be modulated during cancer progression, remission and even treatment. In order to obtain a cellular population enriched in CTCs, various techniques can be used. In one embodiment, it is possible to preferably enrich a cellular population in CTCs using FACS or an immunoadsorption technique for surface markers associated to CTCs prior to any in vitro culture. In order to obtain a population enriched in CTCs, the population enriched in CCCs is submitted to a positive selection for CK-positive cells (e.g. selection of CK-positive cells (and in some embodiments from CK8-positive cells) from the population of CCCs) and/or to a positive selection for EpCAM-positive cells (e.g. selection of EpCAM-positive cells from the populations of CCCs). These positive selections can be made using FACS or immunoadsorption for example. In addition, the order in which the negative and selective selections occurs is irrelevant to obtain the population enriched in CTCs.

Once the initial population enriched in CCCs is obtained, it can be submitted to further selection steps to obtain a population enriched in circulating epithelial mesenchymal transition cells (EMTCs). As indicated above for populations enriched in CCCs, it is believed that the composition of the population of EMTCs will be modulated during cancer progression, remission and even treatment. In order to obtain a cellular population enriched in EMTCs, various techniques can be used. In one embodiment, it is possible to preferably enrich a cellular population in EMTCs using FACS or an immunoadsorption technique for surface markers associated to EMTCs prior to any in vitro culture. In order to obtain a population enriched in EMTCs, the population enriched in CCCs is submitted to a negative selection for CK-positive cells (e.g. removal of CK-positive cells (and in some embodiments from CK8-positive cells) from the population of CCCs) and to a positive selection for vimentin-positive cells (e.g. selection of vimentin-positive cells from the populations of CCCs) as well as a positive selection for N cadherin-positive cells (e.g., selection of N-cadherin-positive cells from the population of CCCs). These positive and negative selections can be made using FACS or immunoadsorption for example. In addition, the order in which the negative and selective selections occurs is irrelevant to obtain the population enriched in EMTCs. The population of EMTCs can be further divided upon the presence or absence of additional markers such as E-cadherin. Some EMTCs subpopulations are E-cadherin-negative (and can be obtained by conducting a negative E-cadherin selection).

Screening Assays Based on Populations Enriched in CCCs, CSCs and/or CTCs

The population of cells obtained by the methods described herein represents, prior to culture, a population of cancer cells specific to a specific period in time and specific to a specific patient. It is believed that the CCCs, CSCs and/or CTCs described herein are representative of cancer status and as such, their characterization can facilitate the selection/design of an appropriate therapeutic regimen. It is also believed that it is possible to obtain longitudinal (with respect to a timeline) populations of CCCs, CSCs and/or CTCs and that the characterization of such longitudinal populations can be used to determine if modifications to therapeutic regimen can provide therapeutic benefits to the patient. Consequently, it is contemplated herewith to use these cells to predict the cancer status of the patients, characterize their respective circulating cancer cells, and subsequently select/design/alter a therapeutic regimen to maximize therapeutic benefits to the patient.

The present disclosure provides predictive applications based on the characterizatrion of populations of CCCs, CSCs and/or CTCs to determine the cancer status of an individual. For example, a screened agent or a specific therapeutic regimen is considered useful if it can decrease the number, proliferation rate and/or viability of cells of the population enriched in CCCs, CSCs and/or CTCs. Alternatively, the screened agent or the therapeutic regimen is not considered useful if fails to show a decrease in the number, the proliferation rate and/or the viability of cells of the population enriched in CCCs, CSCs and/or CTCs.

In screening applications, an agent to be screened can placed in a reaction vessel (usually a cell culture vessels and, in some embodiments, in a low or ultra-low adherent cultured vessel) and is supplemented with the population of cells enriched in CCCs, CSCs and/or CTCs. In the assays, the reaction vessel can be any type of container that can accommodate the maintenance or the culture of the population of cells enriched in CCCs, CSCs and/or CTCs as well as the maintenance of cell number, proliferation rate and viability (in the absence of the screened agent). In some embodiment, it is preferably that the culture of cells allows the formation of mammosphere(s). In one embodiment, the CCCs (or a subpopulation thereof) is cultured in a MammoCult™ medium.

Once the population of cells has been placed in the reaction vessel, it can be optionally combined with a screened agent, and a measurement or value of a parameter of population of cells is made. This assessment may be made directly in the reaction vessel (by using a probe) or on a sample of such reaction vessel. The measurement of the parameter can be made either at the DNA level, the RNA level, the polypeptide level or the cellular level. The measuring step can rely on the addition of a quantifier specific to the parameter to be assessed to the reaction vessel or a sample thereof. In another embodiment, the quantifier can be modified by viable/non-viable, proliferating/non-proliferating cells and provide an indirect measure of the parameter. In an embodiment, the signal of the quantifier can be provided by a label that is either directly or indirectly linked to the quantifier.

Various parameters of population of cells can be measured. In one embodiment, the parameter is the total number of cells and/or the number of CSCs or a subpopulation thereof. In another embodiment, the parameter is associated with the viability of the cell(s) (measure of viability, necrosis and/or apoptosis). In still another embodiment, the parameter is associated with the proliferation rate of the cell(s). The parameter associated with the viability/proliferation of the cell(s) can determined through the characterization of a specific polypeptide or of a combination of specific polypeptides. In such embodiment, the parameter that is measured can be the polypeptide's biological activity, the polypeptide quantity and/or stability. The parameter associated with the proliferation/viability of the cell(s) can be determined through the characterization of a specific nucleotide transcript or a combination of specific nucleotide transcripts. In such embodiment, the parameter can be the level of expression, the promoter/regulator activity associated with this nucleotide transcript and/or stability of the nucleotide transcript. Even though a single parameter is required to enable the characterization of the screened agent, it is also provided that more than one parameter may be measured.

If the measurement of the parameter is performed at the nucleotide level, then the transcription activity of the promoter or regulator associated with a specific nucleotide transcript or a combination of specific nucleotide transcripts can be assessed. This assessment can be made, for example, by using a reporter vector encoding a reporter polypeptide. Upon the addition of the screened agent in the reaction vessel, the promotion of transcription from the promoter or regulator is measured indirectly by measuring the transcription of the reporter polypeptide. Alternatively or complementarily, the stability and/or the expression level of the specific nucleotide transcripts or the combination of specific nucleotide transcripts can be assessed by quantifying the presence/absence as well as amount of the nucleotide transcripts (for example using PCR-based assays, micro-RNA based assays, nucleic acid hybridization).

If the measurement of the parameter is performed at the polypeptide level, an assessment of the specific polypeptide (or combination thereof) expression can be performed. In an embodiment, such assessment is made, for example, through an antibody-based technique (such as a Western blot, an ELISA, flow cytometry or fluorescent-activated cell sorting (FACS)), a lectin-based technique, a micro-array, spectrometry, etc. In addition, an assessment of the specific polypeptide(s) biological activity can be performed.

If the measurement of the parameter is performed at the cellular level, an assessment of cellular viability can be made. In one embodiment, a reagent (for example the Alamar-Blue™ or the Presto Blue® dye) which is transformed in a quantifiable signal if the cells are viable can be used. In another embodiment, a reagent which is specific for apoptotic cells (labeled Annexin V and/or JC-1 dye) can be used.

Once the measurement has been made, it is extracted from the reaction vessel, and the test value of the parameter is compared to a control value.

In an embodiment, the control value is associated with the presence of cancer or a lack of prevention, treatment and/or alleviation of symptoms associated with cancer. In such assay format, it is determined that the screened agent or the therapeutic regimen is useful in the prevention, treatment and/or alleviation of symptoms of a cancer when a decrease in the number, proliferation rate and/or the viability of cells in observed in the population studied when compared to a control. In such embodiment, the test value is considered useful (in the treatment, prevention and/or alleviation of symptoms) when it is lower than the control value. Alternatively, the screened agent or the therapeutic regimen is not considered useful in the prevention, treatment and/or alleviation of symptoms of a cancer when they are not able to decrease (e.g. maintain or increase) the number, proliferation rate and/or the viability of cells in the population studied when compared to a control. In such embodiment, the test value is not considered useful (in the treatment, prevention and/or alleviation of symptoms) when it is equal to or higher than the control value.

In another embodiment, the control value is associated with the absence of cancer (healthy control) or the presence of an ability to prevent, treat and/or alleviate of symptoms associated with cancer. In such assay format, the screened agents or therapeutic regimen is useful in the prevention, treatment and/or alleviation of symptoms of a cancer when they are able to provide a similar number, proliferation rate and/or the viability level in the population studied when compared to a control. In such embodiment, the test value is considered useful (in the treatment, prevention and/or alleviation of symptoms) when it is thus equal to or lower than the control value. Alternatively, the screened agent or the therapeutic regimen is not considered useful in the prevention, treatment and/or alleviation of symptoms of a cancer when they are not able to maintain or decrease the number, proliferation rate and/or the viability of cells in the population studied when compared to a control. In such embodiment, the test value is not considered useful if it is thus higher than the control value.

In an embodiment, the comparison can be made by an individual. In another embodiment, the comparison can be made in a comparison module. Such comparison module may comprise a processor and a memory card to perform an application. The processor may access the memory to retrieve data. The processor may be any device that can perform operations on data. Examples are a central processing unit (CPU), a front-end processor, a microprocessor, a graphics processing unit (PPU/VPU), a physics processing unit (PPU), a digital signal processor and a network processor. The application is coupled to the processor and configured to determine the effect of the agent on the parameter studied with respect to the control value. An output of this comparison may be transmitted to a display device. The memory, accessible by the processor, receives and stores data or any other information generated or used. The memory may be a main memory (such as a high speed Random Access Memory or RAM) or an auxiliary storage unit (such as a hard disk, a floppy disk or a magnetic tape drive). The memory may be any other type of memory (such as a Read-Only Memory or ROM) or optical storage media (such as a videodisc or a compact disc).

Once the comparison between the test value and the control value is made, it is possible to characterize the usefulness of the agent.

In an embodiment, the characterization can be made by an individual. In another embodiment, the characterization can be made with a processor and a memory card to perform an application. The processor may access the memory to retrieve data. The processor may be any device that can perform operations on data. Examples are a central processing unit (CPU), a front-end processor, a microprocessor, a graphics processing unit (PPU/VPU), a physics processing unit (PPU), a digital signal processor and a network processor. The application is coupled to the processor and configured to characterize the agent being screened. An output of this characterization may be transmitted to a display device. The memory, accessible by the processor, receives and stores data or any other information generated or used. The memory may be a main memory (such as a high speed Random Access Memory or RAM) or an auxiliary storage unit (such as a hard disk, a floppy disk or a magnetic tape drive). The memory may be any other type of memory (such as a Read-Only Memory or ROM) or optical storage media (such as a videodisc or a compact disc).

The screening methods described herein can be used to determine an agent's ability to prevent, treat or alleviate the symptoms of a cancer. The premise behind this screening method is that the population of cells are representative of a cancer and an agent capable of limiting their proliferation and/or viability will likely have potential therapeutic effects in the cancer patient from which the cells were obtained.

The present disclosure also provides screening systems for performing the characterization and methods described herein. These systems comprise a reaction vessel for placing the agent and the population of cells, a processor in a computer system, a memory accessible by the processor and an application coupled to the processor. The application or group of applications is(are) configured for receiving a test value of a parameter in the presence of the agent; comparing the test value to a control value and/or characterizing the agent in function of this comparison.

The present disclosure also provides a software product embodied on a computer readable medium. This software product comprises instructions for characterizing the agent according to the methods described herein. The software product comprises a receiving module for receiving a test value of a parameter of a population of cells in the presence of an agent; a comparison module receiving input from the measuring module for determining if the test value is lower than, equal to or higher than a control value; a characterization module receiving input from the comparison module for performing the characterization based on the comparison.

In an embodiment, an application found in the computer system of the system is used in the comparison module. A measuring module extracts/receives information from the reaction vessel with respect to the parameter. The receiving module is coupled to a comparison module which receives the value(s) of the parameter and determines if this value is lower than, equal to or higher than a control value. The comparison module can be coupled to a characterization module. In another embodiment, an application found in the computer system of the system is used in the characterization module. The comparison module is coupled to the characterization module which receives the comparison and performs the characterization based on this comparison.

In a further embodiment, the receiving module, comparison module and characterization module are organized into a single discrete system. In another embodiment, each module is organized into different discrete system. In still a further embodiment, at least two modules are organized into a single discrete system.

Predictive Methods of Drug Sensitivity Using the Populations of Cells Enriched in CCCs, CSCs and CTCs The population of cells obtained by the methods described herein represent a cancer cell population. It is believed that some of the CCCs, CSCs and/or CTCs described herein are associated with the tumorigenic and/or metastatic potential of the tumor. In addition, it is possible to obtain viable populations of CCCs, CSCs and/or CTCs. Consequently, it is contemplated herewith to use these cells to determine the sensitivity of a subject for therapeutic agents. This method can be used to determine, prior to administration, if a therapeutic agent will provide therapeutic benefits to the patient.

The present disclosure provides applications to determine the sensitivity of a cancer patient to a therapeutic agent. The subject is considered sensitive to the therapeutic agent if the latter can decrease the number, proliferation rate and/or viability of cells of the population enriched in CCCs, CSCs and/or CTCs. Alternatively, the subject is not considered sensitive to the therapeutic agent is the latter is not shown to decrease the number, the proliferation rate and/or the viability of cells of the population enriched in CCCs, CSCs and/or CTCs.

In such sensitivity predictive applications, a potential therapeutic agent can be placed in a reaction vessel (usually a cell culture vessel and, in some embodiments, in a low or ultra-low adherent cultured vessel) and is supplemented with the population of cells enriched in CCCs, CSCs and/or CTCs. In the assays, the reaction vessel can be any type of container that can accommodate the culture of the population of cells enriched in CCCs, CSCs and/or CTCs as well as the maintenance of cell number, proliferation rate and viability of the cultured cells in the absence of the screened agent. In some embodiment, it is preferable that the culture of cells allows the formation of mammosphere(s). In embodiments where CCCs, CSCs and/or CTCs are obtained from a breast cancer patient, the following therapeutic agent can be tested: tamoxifen, herceptin, taxol and doxorubicin.

Once the population of cells and the therapeutic agent have been placed in the reaction vessel, a measurement or value of a parameter of population of cells is made. This assessment may be made directly in the reaction vessel (by using a probe) or on a sample of such reaction vessel. The measurement of the parameter can be made either at the DNA level, the RNA level, the polypeptide level or the cellular level. The measuring step can rely on the addition of a quantifier specific to the parameter to be assessed to the reaction vessel or a sample thereof. In another embodiment, the quantifier can be modified by viable/non-viable, proliferating/non-proliferating cells and provide an indirect measure of the parameter. In an embodiment, the signal of the quantifier can be provided by a label that is either directly or indirectly linked to the quantifier.

Various parameters of population of cells can be measured. In one embodiment, the parameter is the total number of cells and/or the number of CSCs or CTCs in the culture. In another embodiment, the parameter is associated with the viability of the cell(s) (measure of viability, necrosis and/or apoptosis). In still another embodiment, the parameter is associated with the proliferation rate of the cell(s). The parameter associated with the viability/proliferation of the cell(s) can determined based on a specific polypeptide or a combination of specific polypeptides. In such embodiment, the parameter that is measured can be the polypeptide's biological activity, the polypeptide quantity and/or stability. The parameter associated with the proliferation/viability of the cell(s) can be determined based on a specific nucleotide transcript or a combination of specific nucleotide transcripts. In such embodiment, the parameter can be the level of expression, the promoter/regulator activity associated with this nucleotide transcript and/or stability of the nucleotide transcript. Even though a single parameter is required to enable the characterization of the cancer subject, it is also provided that more than one parameter may be measured.

If the measurement of the parameter is performed at the nucleotide level, then the transcription activity of the promoter or regulator associated with specific nucleotide transcript or a combination of specific nucleotide transcripts can be assessed. This assessment can be made, for example, by using a reporter vector encoding a reporter polypeptide. Alternatively or complementarily, the stability and/or the expression level of the specific nucleotide transcripts or the combination of specific nucleotide transcripts can be assessed by quantifying the presence/absence as well as amount of the nucleotide transcripts (for example using PCR-based assays, micro-RNA based assays, nucleic acid hybridization).

If the measurement of the parameter is performed at the polypeptide level, an assessment of the specific polypeptide (or combination thereof) expression can be performed. In an embodiment, such assessment is made, for example, through an antibody-based technique (such as a Western blot, an ELISA, flow cytometry or a FACS), a lectin-based technique, a micro-array, spectrometry, etc. In addition, an assessment of the specific polypeptide(s) biological activity can be performed.

If the measurement of the parameter is performed at the cellular level, an assessment of cellular viability can be made. In one embodiment, a reagent (for example the AlamarBlue™ or the Presto Blue® dye) which is transformed in a quantifiable signal if the cells are viable can be used. In another embodiment, a reagent which is specific for apoptotic cells (labeled Annexin V and/or JC-1 dye) can be used.

Once the measurement has been made, it is extracted from the reaction vessel, and the test value of the parameter is compared to a control value.

In an embodiment, the control value is associated with a lack of sensitivity (e.g. a resistance) to the therapeutic agent. In such assay format, tested cancer subject are considered sensitive to the therapeutic agent when the number, proliferation rate and/or the viability of cells is reduced when compared to a control value. In this embodiment, the test value of the cancer subject considered sensitive is thus lower than the control value. Alternatively, tested subjects are not considered sensitive (e.g. they are considered resistant) to the therapeutic agent if the population of cells, in the presence of an agent, does not show a decrease in the number, proliferation rate and/or the viability of cells when compared to a control. In such embodiment, the test value of the tested subject not considered sensitive is thus either equal to or higher than the control value.

In another embodiment, the control value is associated with a sensitivity to a therapeutic agent. In such assay format, tested subjects who provide a test value showing a similar or lower number, proliferation rate and/or the viability when compared to a control are considered sensitive. The test value of the tested subject considered sensitive is thus equal to or lower than the control value. Alternatively, tested subjects who provide a test value showing higher cell number, proliferation rate and/or the viability when compared to the control value are considered to lack sensitivity (e.g. show resistance) to the therapeutic agent. The test value of resistant subject is thus higher than the control value.

In an embodiment, the comparison can be made by an individual. In another embodiment, the comparison can be made in a comparison module. Such comparison module may comprise a processor and a memory card to perform an application. The processor may access the memory to retrieve data. The processor may be any device that can perform operations on data. Examples are a central processing unit (CPU), a front-end processor, a microprocessor, a graphics processing unit (PPU/VPU), a physics processing unit (PPU), a digital signal processor and a network processor. The application is coupled to the processor and configured to determine the effect of the agent on the parameter studied with respect to the control value. An output of this comparison may be transmitted to a display device. The memory, accessible by the processor, receives and stores data or any other information generated or used. The memory may be a main memory (such as a high speed Random Access Memory or RAM) or an auxiliary storage unit (such as a hard disk, a floppy disk or a magnetic tape drive). The memory may be any other type of memory (such as a Read-Only Memory or ROM) or optical storage media (such as a videodisc or a compact disc).

Once the comparison between the test value and the control value is made, it is possible to characterize the usefulness of the agent.

In an embodiment, the characterization can be made by an individual. In another embodiment, the characterization can be made with a processor and a memory card to perform an application. The processor may access the memory to retrieve data. The processor may be any device that can perform operations on data. Examples are a central processing unit (CPU), a front-end processor, a microprocessor, a graphics processing unit (PPU/VPU), a physics processing unit (PPU), a digital signal processor and a network processor. The application is coupled to the processor and configured to characterize the tested subject. An output of this characterization may be transmitted to a display device. The memory, accessible by the processor, receives and stores data or any other information generated or used. The memory may be a main memory (such as a high speed Random Access Memory or RAM) or an auxiliary storage unit (such as a hard disk, a floppy disk or a magnetic tape drive). The memory may be any other type of memory (such as a Read-Only Memory or ROM) or optical storage media (such as a videodisc or a compact disc).

The predictive methods described herein can be used to determine the sensitivity of a cancer subject to a therapeutic agent. The premise behind this predictive method is that the population of cells are representative of a cancer and an agent capability of limiting their proliferation and/or viability will likely have therapeutic effects in a cancer patient. The predictive method can be performed prior to the administration of the therapeutic agent to determine if the subject will be sensitive to the therapeutic agent. Alternatively, the predictive method can be performed after the administration of at least one dose of a therapeutic agent to determine if the subject remains sensitive to the therapeutic agent or shows resistance to the therapeutic agent. In some embodiments, the predictive method can be performed at a predetermined period (e.g., one year) after the administration of the at least one dose of the therapeutic agent to determine if the cancer subject has developed resistance to the therapeutic agent.

The present disclosure also provides systems for performing the characterization and methods described herein. These systems comprise a reaction vessel for placing the agent and the population of cells, a processor in a computer system, a memory accessible by the processor and an application coupled to the processor. The application or group of applications is(are) configured for receiving a test value of a parameter in the presence of the agent; comparing the test value to a control value and/or characterizing the subject in function of this comparison.

The present disclosure also provides a software product embodied on a computer readable medium. This software product comprises instructions for characterizing the agent according to the methods described herein. The software product comprises a receiving module for receiving a test value of a parameter of a population of cells in the presence of an agent; a comparison module receiving input from the measuring module for determining if the test value is lower than, equal to or higher than a control value; a characterization module receiving input from the comparison module for performing the characterization based on the comparison.

In an embodiment, an application found in the computer system of the system is used in the comparison module. A measuring module extracts/receives information from the reaction vessel with respect to the parameter. The receiving module is coupled to a comparison module which receives the value(s) of the parameter and determines if this value is lower than, equal to or higher than a control value. The comparison module can be coupled to a characterization module. In another embodiment, an application found in the computer system of the system is used in the characterization module. The comparison module is coupled to the characterization module which receives the comparison and performs the characterization based on this comparison.

In a further embodiment, the receiving module, comparison module and characterization module are organized into a single discrete system. In another embodiment, each module is organized into different discrete system. In still a further embodiment, at least two modules are organized into a single discrete system.

Predictive Methods Based on the Characterization of Populations of Cells Enriched in CCCs, CSCs and/or CTCs The population of cells obtained by the methods described herein represents a cancer cell population and in some embodiments, it can reflect some of the biological aspect of the cancer. It is believed that some of the CCCs, CSCs and/or CTCs described herein are associated with the tumorigenic and/or metastatic potential of the tumor. Consequently, it is contemplated herewith to characterize these cells to determine the cancer status of a subject. Such cancer status can be determined in a longitudinal fashion to monitor cancer progression and/or remission, drug sensitivity/resistance, chemokine receptor status, etc. The cancer status can be used to select/design/alter treatment regimen to maximize the therapeutic benefits to the patients.

A first population of cells enriched in CCCs, CSCs and/or CTCs is provided in a reaction vessel. This first population of cells can be a fresh uncultured one or it can be submitted to a culturing step prior to the undertaking of this method. Once the population of cells and the agent have been placed in the reaction vessel, a measurement or value of at least one cancer marker parameter is obtained. This assessment may be made directly in the reaction vessel (by using a probe) or on a sample of such reaction vessel. The measurement of the parameter can be made either at the DNA level, the RNA level, the polypeptide level or the cellular level.

One of the cancer marker that can be monitored is the expression cell surface receptors that can be used to stratify patients. It can be used to determine to which subgroup the patient is stratified and if this classification remains or changes in time. For example, in breast cancer patients, the expression of surface receptors HER2, ER and/or PR is currently used to stratify patients into the triple negative group (HER2−, ER−, PR−); the luminal A group (HER2−, ER+, PR+); the luminal B group (HER2−, ER+, PR−); and the Her2 group (HER2+, ER+/−, PR+/−). In another example, in melanoma patients, the expression of the following markers (alone or in combination) can be used: GP100, MART1 (MELA-A), tyrosinase, S100 and melanoma-associated chondroitin sulfate proteoglycan (MCSP). In still another example, in prostate patient, the prostate-specific antigen (PSA), also known as gamma-seminoprotein or kallikrein-3 (KLK3), can be used as a marker. As such stratification-associated markers include, but are not limited to Her2, ER, PR, GP100, MART1, tyrosinase, S100, MCSP and/or PSA as well as any combination thereof.

Another cancer marker that can be monitored is the expression of polypeptides (or their associated nucleotide transcripts) associated with drug sensitivity or resistance. This cancer marker can be used to determine the overall drug sensitivity/resistance phenotype of the cancer and if this sensitivity/resistance remains or changes in time. Drug sensitivity/resistance markers include, but are not limited to phosphoPI3K, Akt1 (total and phosphorylated form), Akt2, Bcl2 (associated with an anti-apoptotic phenotype), cyclin D1 (associated with cellular proliferation) and/or Ki67 (associated with cellular proliferation).

A further cancer marker that can be monitored is the expression of chemokine receptors associated with the predisposition to specific metastatic sites. This cancer marker can be used to determine the metastatic potential and/or the metastatic homing site and if this metastatic potential remains or changes in time. Metastatic-associated cancer marker include, but are not limited to CXCR4 (associated with bone metastasis), CX3R1 (associated with brain metastasis), CCR7 (associated with lymph node metastasis) and/or CCR6 (associated with inflammatory sites metastasis).

Yet another cancer marker that can be monitored is the total number of CCCs, the total number of CSCs or the total number of CTCs as well as ratio amongst these cell numbers. It is believed that a reduction in the total number or CCCs or a reduction in the ratio of CSCs/CCCs or CSCs/CTCs is associated with a good prognosis.

Still another cancer marker that can be monitored is a polypeptide or a combination of polypeptides (or their associated nucleotide transcript(s)) known to be associated to a particular cancer state.

In the methods described herein, a single cancer marker or a combination of cancer markers can be used. Optionally, CCCs, CTCs or CSCs-specific marker can be used in combination to cancer markers to determine which cellular population express which cancer marker and provide further specificity to the cancer status.

The measuring step can rely on the addition of a quantifier specific to the parameter to be assessed to the reaction vessel or a sample thereof. In another embodiment, the quantifier can be modified by cells of the population studied to provide an indirect measure of the cancer marker. In an embodiment, the signal of the quantifier can be provided by a label that is either directly or indirectly linked to the quantifier.

The parameter associated with cancer marker can be a specific polypeptide or a combination of specific polypeptides. In such embodiment, the parameter that is measured can be the polypeptide's biological activity, the polypeptide quantity and/or stability. The parameter associated with the cancer marker can be a specific nucleotide transcript or a combination of specific nucleotide transcripts. In such embodiment, the parameter can be the level of expression, the promoter/regulator activity associated with this nucleotide transcript and/or stability of the nucleotide transcript. Even though a single parameter is required to enable the characterization of the cancer status, it is also provided that more than one parameter may be measured and that, in some embodiment, an array maybe performed.

If the measurement of the value is obtained at the nucleotide level, then the transcription activity of the promoter or regulator associated with specific nucleotide transcript or a combination of specific nucleotide transcripts can be assessed. This assessment can be made, for example, by using a reporter vector encoding a reporter polypeptide. Alternatively or complementarily, the stability and/or the expression level of the specific nucleotide transcripts or the combination of specific nucleotide transcripts can be assessed by quantifying the presence/absence as well as amount of the nucleotide transcripts (for example using PCR-based assays, RNA/cDNA-assay based assays, nucleic acid hybridization, etc.).

If the measurement of the value is obtained at the polypeptide level, an assessment of the specific polypeptide (or combination thereof) expression can be performed. In an embodiment, such assessment is made, for example, through an antibody-based technique (such as a Western blot, an ELISA, flow cytometry or a FACS), a lectin-based technique, a microarray, spectrometry, etc. In addition, an assessment of the specific polypeptide(s) biological activity can be performed.

Once the measurement has been made, it is used to characterize the cancer status. In one embodiment the cancer status is a cancer subgroup/subclass and can be determined, for example, based on the expression of surface receptors. In another embodiment, the cancer status is a predisposition to form a metastasis (and in further embodiments to form a metastasis at a specific site) and can be determined, for example, based on the expression of chemokine receptors. In yet another embodiment, the cancer status is a sensitivity or a resistance to a therapeutic agent.

In some instances, a second test value of a population of cells obtained from a patient at a later point in time can be obtained. The population of cells from which the second test value is obtained can be the same type of cells (CCCs, CSCs, CTCs or combinations thereof) that the population of cells from which the first test value is obtained. In one embodiment, the first test value is from a population of cells obtained from a subject prior to the administration of a first dose of a therapeutic agent and the second test value is from a population of cells obtained from a subject after to the administration of a first dose of a therapeutic agent. In another embodiment, the first test value is from a population of cells obtained from a subject prior to the administration of a dose of a therapeutic agent and the second test value is from a population of cells obtained from a subject after to the administration of the dose of a therapeutic agent. The population of cells from which the second test value is obtained can be a different type of cells (CCCs, CSCs, CTCs or combinations thereof) that the population of cells from which the first test value is obtained. The second test value is compared to the first test value to provide a longitudinal characterization of the cancer status of the patient. Additional test values, obtained at different point in time, can also be used to provide a prolonged longitudinal characterization of the cancer status of the patient.

In other embodiment, the second test value is obtained from (a sample of) the (primary) tumor or a metastasis of the patient. The second test value is compared to the first test value to provide a longitudinal characterization of the cancer status of the patient. Additional test values, obtained at different point in time, can also be used to provide a prolonged longitudinal characterization of the cancer status of the patient.

In an embodiment, the comparison can be made by an individual. In another embodiment, the comparison can be made in a comparison module. Such comparison module may comprise a processor and a memory card to perform an application. The processor may access the memory to retrieve data. The processor may be any device that can perform operations on data. Examples are a central processing unit (CPU), a front-end processor, a microprocessor, a graphics processing unit (PPU/VPU), a physics processing unit (PPU), a digital signal processor and a network processor. The application is coupled to the processor and configured to determine the cancer status. An output of this comparison may be transmitted to a display device. The memory, accessible by the processor, receives and stores data or any other information generated or used. The memory may be a main memory (such as a high speed Random Access Memory or RAM) or an auxiliary storage unit (such as a hard disk, a floppy disk or a magnetic tape drive). The memory may be any other type of memory (such as a Read-Only Memory or ROM) or optical storage media (such as a videodisc or a compact disc).

Once the first test value is obtained or a comparison between the first and second test value is done, the characterization of the cancer status can be made. In an embodiment, the characterization can be made by an individual. In another embodiment, the characterization can be made with a processor and a memory card to perform an application. The processor may access the memory to retrieve data. The processor may be any device that can perform operations on data. Examples are a central processing unit (CPU), a front-end processor, a microprocessor, a graphics processing unit (PPU/VPU), a physics processing unit (PPU), a digital signal processor and a network processor. The application is coupled to the processor and configured to characterize the cancer status. An output of this characterization may be transmitted to a display device. The memory, accessible by the processor, receives and stores data or any other information generated or used. The memory may be a main memory (such as a high speed Random Access Memory or RAM) or an auxiliary storage unit (such as a hard disk, a floppy disk or a magnetic tape drive). The memory may be any other type of memory (such as a Read-Only Memory or ROM) or optical storage media (such as a videodisc or a compact disc).

The predictive methods described herein can be used to characterize the cancer status of a patient. The premise behind this predictive method is that the populations of cells are representative of cancer status and that characterizing the population of cells with a cancer marker will provide valuable information on the cancer status. The predictive method can be performed prior to the administration of the therapeutic agent to determine if the subject is sensitive/resistant to the therapeutic agent. Alternatively, the predictive method can be performed after the administration of at least one dose of a therapeutic agent to determine if the subject remains sensitive to the therapeutic agent or shows resistance to the therapeutic agent. In some embodiments, the predictive method can be performed after the surgical removal of a tumor. The predictive method can be performed to characterize the metastatic potential of the cancer. The predictive method can be performed to stratify patients according to subclasses.

The present application also provides systems for performing the characterization and methods described herein. These systems comprise a reaction vessel for placing the agent and the population of cells, a processor in a computer system, a memory accessible by the processor and an application coupled to the processor. The application or group of applications is(are) configured for receiving a test value of a cancer marker; optionally comparing the test value to a further test value and/or characterizing the cancer status.

The present application also provides a software product embodied on a computer readable medium. This software product comprises instructions for characterizing the agent according to the methods described herein. The software product comprises a receiving module for receiving a test value of a cancer marker; an optional comparison module receiving input from the measuring module; a characterization module receiving input from the measuring module or the comparison module for performing the characterization.

In an embodiment, an application found in the computer system of the system is used in the comparison module. A measuring module extracts/receives information from the reaction vessel with respect to the cancer marker. The receiving module can be coupled to an optional comparison module which receives the value(s) of the parameter and determines if this value is lower than, equal to or higher than a further test value. The measuring module or the comparison module can be coupled to a characterization module. In another embodiment, an application found in the computer system of the system is used in the characterization module. The measuring module is coupled to the characterization module and performs the characterization. The comparison module is coupled to the characterization module which receives the comparison and performs the characterization based on this comparison.

In a further embodiment, the receiving module, comparison module and characterization module are organized into a single discrete system. In another embodiment, each module is organized into different discrete system. In still a further embodiment, at least two modules are organized into a single discrete system.

The present invention will be more readily understood by referring to the following examples which are given to illustrate the invention rather than to limit its scope.

Example I

CCC-Enrichment from Apheresis Product

Screening.

Cancer patients were first screened using 10 mL of peripheral blood followed by a Ficoll™ gradient (according to the manufacturer's instructions) to collect peripheral blood mononuclear cells (PBMCs). The PBMCs were then enriched in CCCs using a negative selection (RoboSep™) with magnetic beads coated with anti-CD45 specific antibodies (StemCell Technologies, Vancouver, BC). The CD45-negative fraction obtained is referred herein as the peripheral blood (PB)-enriched CCCs. Cells were examined by immunohistochemistry following a Cytospin™ concentration and staining with cytokeratin using the Epimet™ detection kit (AS Diagnostic, Germany). Patients classified as CTC-positive (based on Epimet™-positive staining) were selected for the apheresis procedure.

Semi-Purified CTCs from Apheresis Product.

Apheresis is conducted on screened patients as well as on normal subjects to obtain apheresis product (APP). The configuration on the machine is to be pre-set to MNC (mononuclear cells) collection where the default endpoint for MNC procedures is 2.0×TBV of the patient, where TBV is the total blood volume [TBV for males=$0.3669*(Ht\ in\ M)^3+0.03219*(Wt\ in\ kgs)+0.6041$ and for females=$0.3561*(Ht\ in\ M)^3+0.03308\times(Wt\ in\ kgs)+0.1833$]. Also the MNC inlet:AC Ratio should be 12:1, where AC stands for anticoagulant. The AC infusion rate should be 0.8 mL/min/L of TBV. In regards to the collection flow rate, for MNC collection it has to be 1.0 mL/min. After the patient's information has been entered into the machine, the patient is connected through a venipuncture access and return sites. The Collect Volume is 200 mL. When the machine starts, a WBC Colorgram is used to help determine when the hematocrit (Hct) of the product in the collect line is correct (for MNC procedures the collection should be at an Hct of 2% to 4% on the Colorgram). If the color is too dark, the plasma pump flow rate should be decreased at a rate of 0.3-1.0 mL/min every 3-5 minutes. If it is too light, the plasma pump flow rate should be increased by the same adjustments. When the Collect Volume is reached, the patient is disconnected and the plasma bad sample is taken for further handling. First, the 200 mL ($3\times10^9$ nucleated cells) of the APP were applied to a Ficoll gradient (according to the manufacturer's specifications) to concentrate nucleated cells into a volume of 80 to 100 mL. Then, 25 to 30 mL of the concentrated nucleated cells, containing about $10^9$ nucleated cells, were incubated with magnetic beads coated with anti-CD45 specific antibodies using the Robosep™ technology (StemCell Technologies, Vancouver, BC). The CD45-negative fraction (15 to 20 mL containing about $10^8$ nucleated cells) containing tumor cells was collected and is herein referred to as the APP-enriched CTCs. This negative selection process with RoboSep™ permitted a 10-fold enrichment of circulating tumor cells in the collected (e.g. APP-enriched) fraction. An aliquot of the enriched fraction is applied to a glass slide using Cytospin™ and stained cytokeratin using the Epimet™ detection kit. The remaining enriched fraction is then aliquoted (15 to 20 aliquots containing around $5\times10^6$ nucleated cells/aliquot). Each aliquot contains between 1 000 to 3 000 CTCs and is preserved at ultra low temperature.

Using this technique, up to $10^5$ cytokeratin-positive cells we successfully collected (calculated from Epimet™-positive cells) from a single apheresis sample. Previous studies on CCC enrichment have obtained about 100 cells/sample.

ANCP from healthy volunteers was subjected to the same procedure as described above. Briefly, following apheresis, APP is concentrated using a Ficoll™ gradient and semi-purified with a CD45 RoboSep™ selection. The negative and positive RoboSep™ fractions are collected, aliquoted and preserved at ultra low temperature. The ANCP-enriched cells obtained from healthy volunteers do not contain Epimet™-positive cells. Optionally, the semi-purified fractions can be spiked with tumor cells (e.g. human cell lines such as MCF7). It is also use as a negative control for FACS and other experiments.

Antibodies.

An anti-pan-cytokeratin monoclonal antibody A45-B/B3 (Epimet™ detection kit, AS Diagnostic, Germany) was used to allow positive visual identification of OTCs and approximate estimation of the total number of OTCs. An anti-CD24 antibody (ab19704, Abcam) was used to allow identification of ductal phenotype as well as the stem cell phenotype. An anti-CD44 antibody (M7082, DAKO) was used to allow identification of the stem cell phenotype. An anti-E-cadherin antibody (18-0223; Invitrogen) was used to allow identification of invasive phenotype. An anti-C-X-C chemokine receptor type 4 (CXCR4) antibody (ab2074; Abcam) was used to allow identification of bone homing phenotype. An anti-cytokeratin 8 (CK8) antibody (GP11; progen biotechnik) was used to confirm the epithelial phenotype. An anti-aldehyde dehydrogenase 1 (ALDH1) antibody (ab23375; Abcam) was used to allow identification of stem cell phenotype. An anti-epithelial cell adhesion molecule (EpCAM) antibody (10109; StemCell Technologies) was used to allow differentiation between OTCs and CSCs. An anti-ERa antibody was used to allow the identification of ER-positive and ER-negative cells. An anti-vimentin antibody was used to allow the identification of epidermal-mesenchymal transition cells. In some instances, the cell nucleus was stained with DAPI.

Fluorescence-Activated Cell Sorting (FACS).

FACS was done using both anti-CD45 antibodies and anti-epithelial cell adhesion molecule antibodies (EpCAM) to determine the percentage of OTCs in the apheresis semi-purified fraction. A substantial number of CTCs do not express EpCAM and this number varies from patient to patient. Following FACS, cell sorting of both CD45 negative/EpCAM positive and negative fractions is done and flow-through fractions are collected and preserved at ultra low temperature.

Cell Culture.

Aliquots of CD45-negative cell population were grown in stem cell media or mammocult media (both from StemCell Technologies, Vancouver BC). Briefly, a frozen aliquot (1 mL) of RoboSep™ CD45-negative cell population (as described above and containing about $5\times10^6$ nucleated cells and about 1 000 to 3 000 CCCs based on Epimet™-positive staining). The culture media is changed at various timed intervals.

During culture, the stem cells can form spheres. When the spheres reach approximately 60 µm (containing 20-30 cells), they are submitted to a passage. Briefly, the cell suspension is centrifuged in a 15 mL conical. The supernatant (e.g., used media) is removed and resuspended in 0.5 to 1 mL of pre-warmed 1% Trypsin-EDTA (Invitrogen) is added. The cells are incubated at 37° C. for 10 min, the reaction is stopped by adding 2-5 mL of DMEM 10% FBS, and the cell suspension centrifuged at 350×g for 5 minutes, rinsed with 20-30 mL PBS, centrifuged at 350×g for 5 minutes and finally resuspended in 3 mL of MammoCult™ medium and cultured as described above in ultra-low attachment plates. At passage 2, 4 and 6, cells are collected for further characterization and for determination of stability using. Cells were cultured for up to 6 passages and a 100 to 200-fold expansion of the initial cell population was reached (approximately 200 000 to 600 000 cells from an initial seeding of 1000 to 3000 CTCs). Alternatively, cells are grown attached in adherent culture dishes or plates in MammoCult™ media. In these culture conditions cell expansion is limited to two-three passages with a total number of cells of 100 000-200 000 obtained from one single frozen aliquot.

$RT^2$-PCR.

TABLE 1

Characteristics of the subjects whose CCCs were further characterized by $RT^2$-PCR.

| Subject ID | Stage | Initial Diagnosis | $1^{st}$ metastatic site | Estrogen receptor | Progesterone receptor | Her2 neu |
|---|---|---|---|---|---|---|
| BC0008 | III | Invasive Ductal Carcinoma | No mets | + | + | 3+ |
| BC0013 | Metastatic | Invasive Lobular Carcinoma | Bone and Liver | + | − | − |
| BC0019 | III | Invasive Ductal Carcinoma | No mets | + | + | − |

Animal Study.

Mammospheres from CCCs-enriched cellular population were injected into the bone marrow of a SCID mouse. Mice were injected into the right tibia with 10 000 cultured ANCP-enriched CCCs suspended in 50 microliters of sterile PBS. Prior to tumour cell injection the mice were anesthetised with mouse cocktail (ketamine 100 mg/kg, xylazine 10 mg/kg, acepromazine 3 mg/kg).

Example II

Cellular Population Characterization

Late stage breast cancer patients that were enrolled screening positively for Epimet™. Twenty-seven (27) patients underwent apheresis. The cytokeratin-positive CTCs (as identified using Epimet™) from the APP from these patients ranged from 9 000 to 110 000 CTCs/APP.

Figures 1C, 1D:
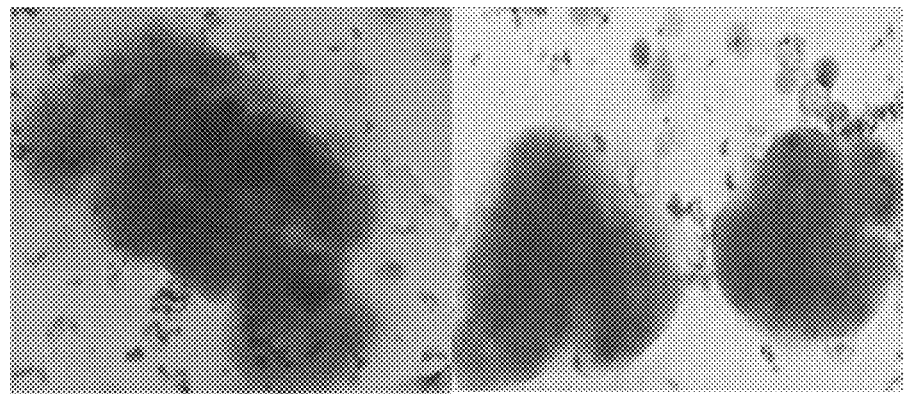
Figures 2A, 2B, 2C:
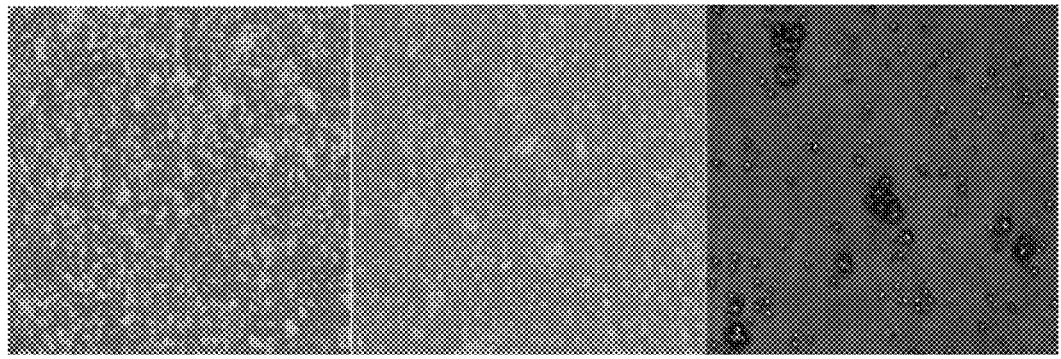
FIG. 2 shows representatives pictures of ANCP-enriched CCCs cultured in non-adherent conditions using the MammoCult™ media. (A) Day 1 (magnification 10×), (B) day 5 (magnification 10×), (C) day 14 (magnification 20×). The appearance of mammospheres are indicated by the arrows in panel C. Immunofluorescence staining of the cultured mammospheres showing (D) positive staining for DAPI and (E) positive staining for ALDH1. These results indicate that the resulting cultured CCCs comprise ALDH1-positive nucleated cells.

Some of the PB-enriched CCCs as well as some of the ANCP-enriched CTCs stained positive for Epimet™ (FIG. 1). The ANCP-enriched CCCs can be cultured as monolayers (using the stem cell media). Alternatively, the APP-enriched CTCs can be cultured or in non-adherent conditions in MammoCult™ media (FIGS. 2A and 2B) and can form mammospheres (FIG. 2C).

Preliminary characterization in mammosphere culture indicates that these cells stain positively for ALDH1, negatively for cytokeratin (CK8) and harbor the CD44(+), CD24 (−) phenotype characteristic of CSCs (data not shown). Six (6) passages in mammocultures on a selected number of patients were successfully achieved without evidence of diminished growth capacity. In contrast, cells grown as attached cells in serum-free medium (stem cell media) stained positively for cytokeratin but had limited growth capacity in vitro (2 to 3 passages). Cell viability was assessed prior to and following liquid nitrogen preservation and indicates that the majority of cells were viable upon thawing and can likely be preserved for long-term banking. The number of isolated CTCs estimated from cytokeratin staining and flow cytometry ranges from a total of 100 000 to 300 000 cells per patient. It is estimated that the number of CSCs likely represents about 10% of the total CTCs population.

The APP-enriched CCCs can be obtained, frozen and thawed without substantially altering their viability (data not shown).

Figures 2D, 2E:
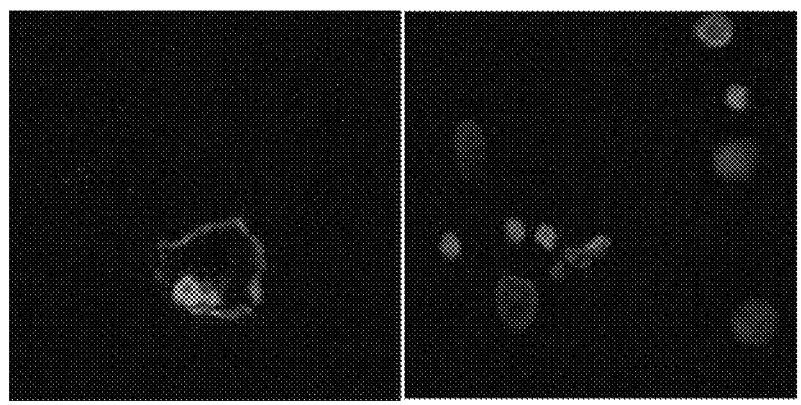
Figures 3A, 3B:
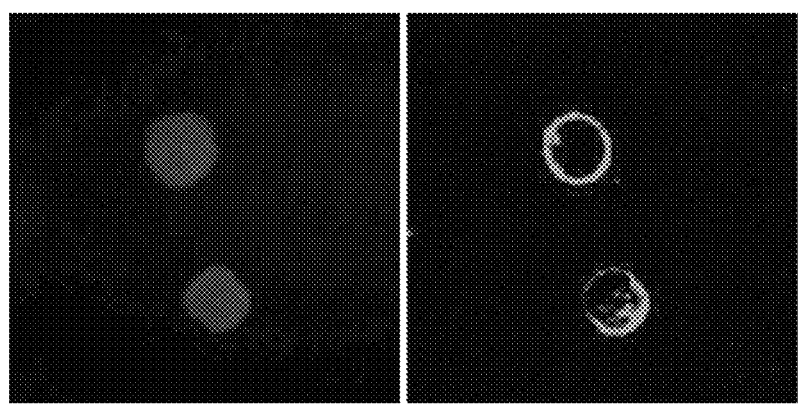
FIG. 3 shows a representative immunofluorescence of ANCP-enriched cultured CCCs using (A) DAPI and (B) an anti-CD44 antibody. These results indicate that the CCCs comprise CD44-positive nucleated cells.
Figures 7A, 7B, 7C:
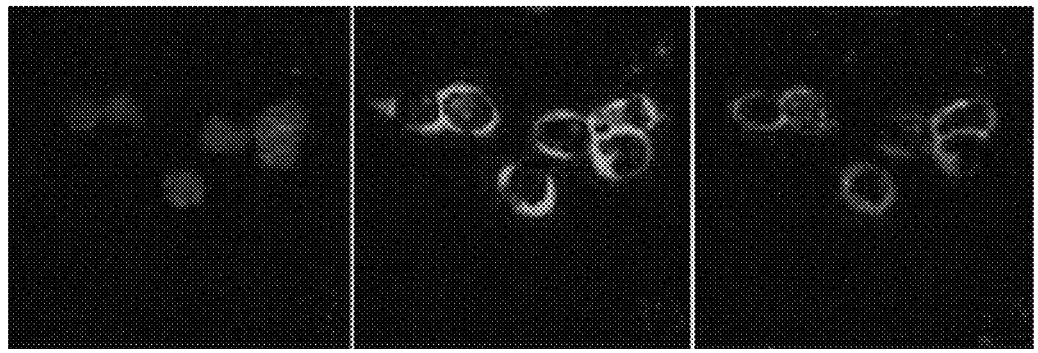
FIG. 7 shows a representative immunofluorescence of ANCP-enriched non-cultured CCCs using (A) DAPI, (B) an anti-ALDH1 antibody and (C) an anti-CK8 antibody. These results indicate that the non-cultured CCCs comprise CK8-positive/ALDH1-positive nucleated cells.

The APP-enriched CCCs were screened for the expression of ALDH1 (a marker of stem-cell like phenotype). Some of the enriched cells (which have not been submitted to culture) are positive for ALDH1 (FIG. 7). In addition, as shown in FIGS. 2D and 2E, some of the cells of the cultured mammospheres also stain positively to ALDH1. In both FIGS. 2 and 7, the same cells stain positively for CK8 confirming their epithelial nature.

The PB-enriched CCCs from a patient with ductal carcinoma were screened for the expression of CD44. Some of the cells of PB-enriched non-cultured and cultured CTCs stain positive for CD44 and represent the ductal phenotype (data not shown). The same cells stain positively for CK8, confirming their epithelial nature (data not shown).

The APP-enriched CTCs from a patient with invasive carcinoma were screened for the expression of E-cadherin (a marker of invasiveness). As shown in FIG. 4, some of the enriched cells of the APP-enriched CTCs stain positive for E-cadherin. The same cells stain positively for CK8, confirming their epithelial nature.

The APP-enriched CTCs from a patient with bone metastasis were screened for the expression of CXCR4. As shown in FIGS. 5 and 6, some of the cells of the APP-enriched CTCs stain positive for CXCR4. The same cells stain positively for CK8, confirming their epithelial nature. Cytokeratin, CD24, CXCR4 and DAPI staining respectively indicate that the cells are epithelial, of breast ductal tissue origin, have bone-homing potency and contain a nucleus.

Figures 8A, 8B, 8C:
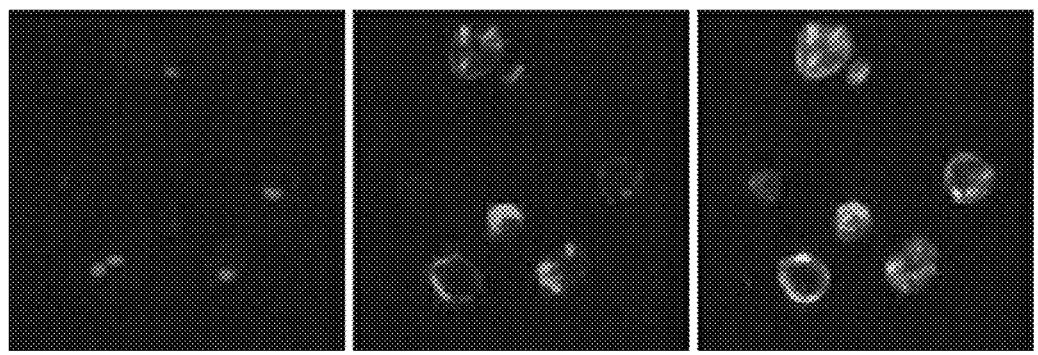
FIG. 8 shows a representative immunofluorescence of ANCP-enriched cultured CCCs using (A) DAPI, (B) an anti-CK8 antibody and (C) an anti-vimentin antibody. These results indicate that the CCCs comprise CK8-positive/vimentin-positive nucleated cells. Panels (D), (E) and (F) show a representative immunofluorescence of ANCP-enriched non-cultured CCCs using DAPI, an anti-CK8 antibody and an anti-vimentin antibody
Figures 8D, 8E, 8F:
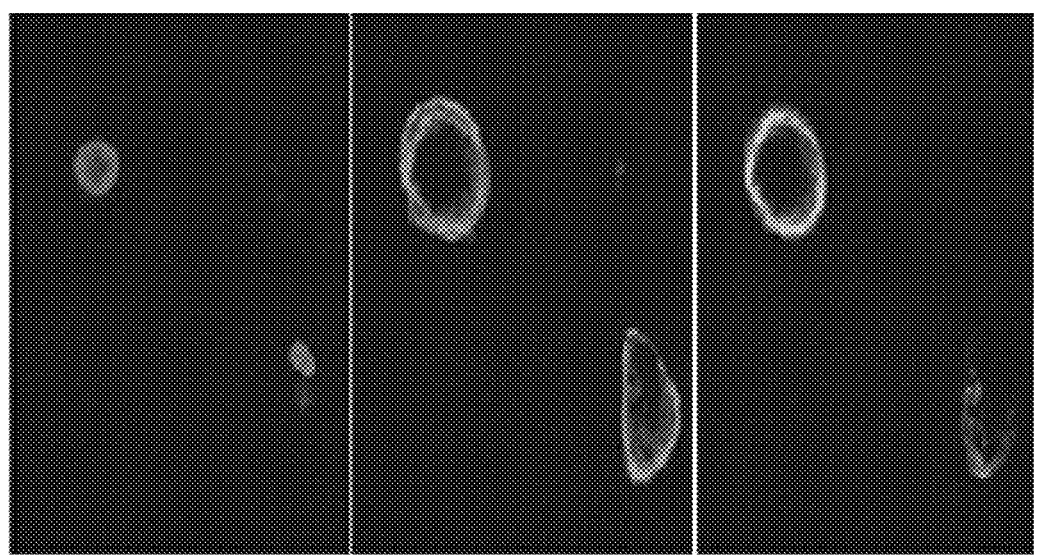

The APP-enriched CCCs from a patient were screened for the expression of vimentin. As shown in FIGS. 8A to 8C, some of the cultured cells of the APP-enriched cells stain positive for vimentin suggesting the presence of an epidermal-mesenchymal transition cell. As shown in FIGS. 8D to 8F, some of the enriched cells also stain positive for vimentin.

The methodology described here offers a distinct advantage over current technologies. It also allows for the collection of clumps (FIG. 9) and the ability to grow and expand CTCs in vitro. Furthermore, some of the CTCs also demonstrate breast cancer stem cell characteristics, the ability to replicate for multiple passages as mammospheres in suspension as well as the maintenance of a metastatic signature.

Figure 11:
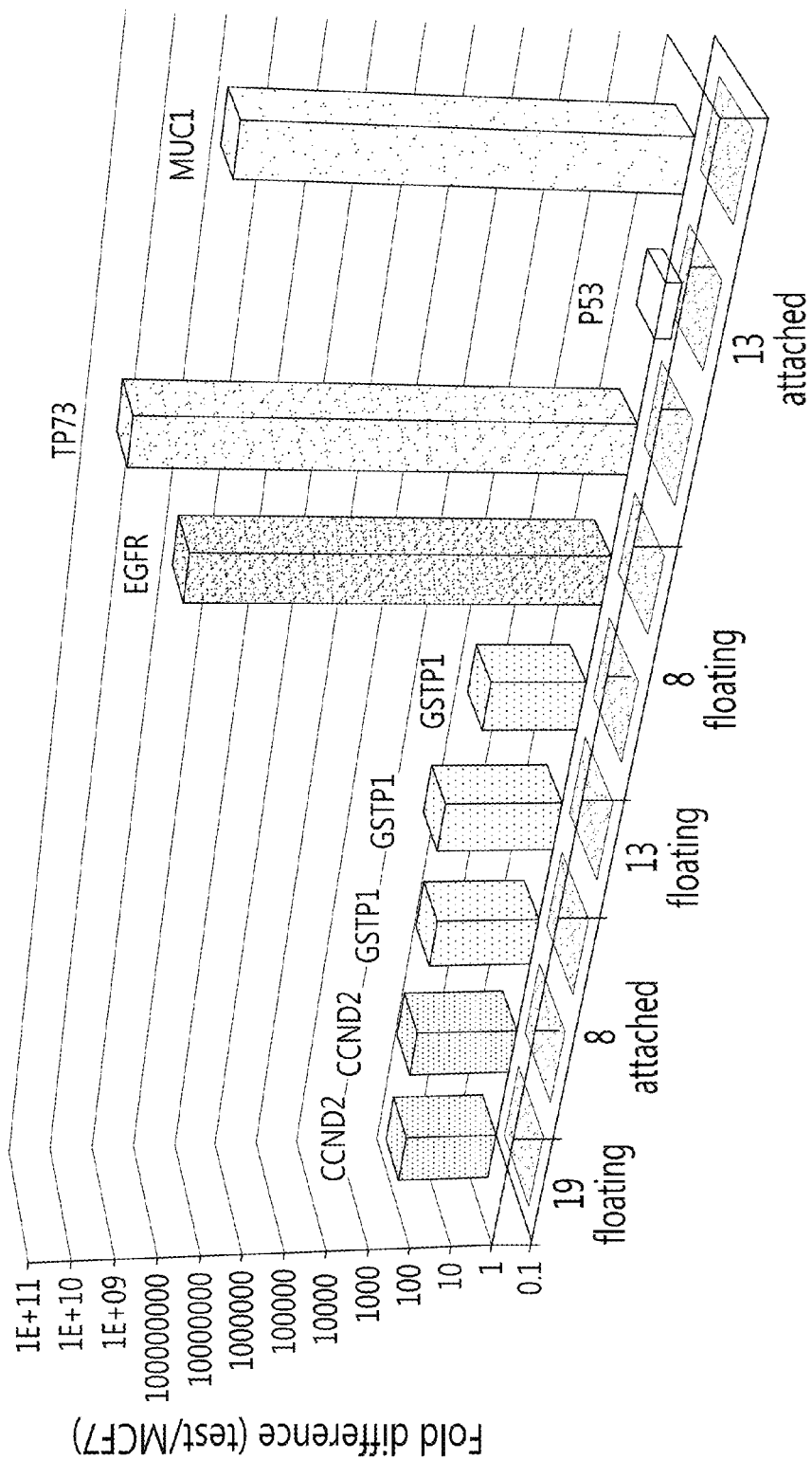
FIG. 11 shows a histogram comparing the fold difference (when compared to MCF7) in the expression of CCND2, GSTP1, EGFR, TP73, P53 and MUC1 genes in CCCs (cultured in either attached conditions or floating conditions) obtained from three different donors (BC0008, BC0013 and BC0019).

The expression of some genes of the cultured cells was further examined. Such results indicate that the overexpression of genes involved in cell cycle, such as cyclin D2, xenobiotic metabolism, like glutathione S-transferase was detected (FIG. 11). It was also determined that neoplasticity markers such as Mucin1 and TP73 were also highly expressed (FIG. 11).

The post-apheresis content of cells from a healthy donor and two breast cancer patients were characterized by flow cytometry. Briefly, the cells were obtained from apheresis and characterized by flow cytometry for their expression of CD45, CK8 and ALDH1. The results are provided in Table 2.

TABLE 2

Cellular characterization of cellular population obtained from apheresis.

| Number or type of cells | Healthy volunteer | Patient A - triple negative, early stage (before chemotherapy) | Patient B - triple negative, late stage (metastatic) |
|---|---|---|---|
| Total number of cells obtained from apheresis | $22 \times 10^6$ | $200 \times 10^6$ | $50 \times 10^6$ |
| Total number of viable cells obtained from apheresis | $17 \times 10^6$ | $195 \times 10^6$ | $45 \times 10^6$ |
| Total CD45$^+$ cells | $16 \times 10^6$ | $193 \times 10^6$ | $45 \times 10^6$ |
| CD45$^+$/CK8$^+$ cells | 20 000 | 79 545 | 37 236 |
| CD45$^+$/CK8$^+$/ALDH1$^+$ cells | 23 | N.D. | 269 |
| CD45$^+$/CK8$^+$/ALDH1$^-$ cells | 1181 | N.D. | 928 |
| CD45$^+$/CK8$^-$ cells | 500 000 | $5 \times 10^6$ | $5 \times 10^6$ |
| CD45$^+$/CK8$^-$/ALDH1$^+$ cells | 50 000 | N.D. | 44 218 |
| CD45$^+$/CK8$^-$/ALDH1$^-$ cells | 300 000 | N.D. | 83 343 |
| Total CD45$^-$ cells | 50 000 | $2 \times 10^6$ | 300 000 |
| CD45$^-$/CK8$^+$ cells | 31 | 663 - identified as CCCs | 456 - identified as CCCs |
| CD45$^-$/CK8$^+$/ALDH1$^+$ cells | None | N.D. | N.D. |
| CD45$^-$/CK8$^+$/ALDH1$^-$ cells | None | N.D. | N.D. |
| CD45$^-$/CK8$^-$ cells | 50 000 | 192 708 - identified as a mixture of EMT and bone cells | 275 968 |
| CD45$^-$/CK8$^-$/ALDH1$^+$ cells | 475 | N.D. | 2 282 - identified as EMT cells |
| CD45$^-$/CK8$^-$/ALDH1$^-$ cells | 2215 - identified as circulating bone cells | N.D. | 3 270 - identified as circulating bone cells |

N.D. = not determined.

Figure 12D:
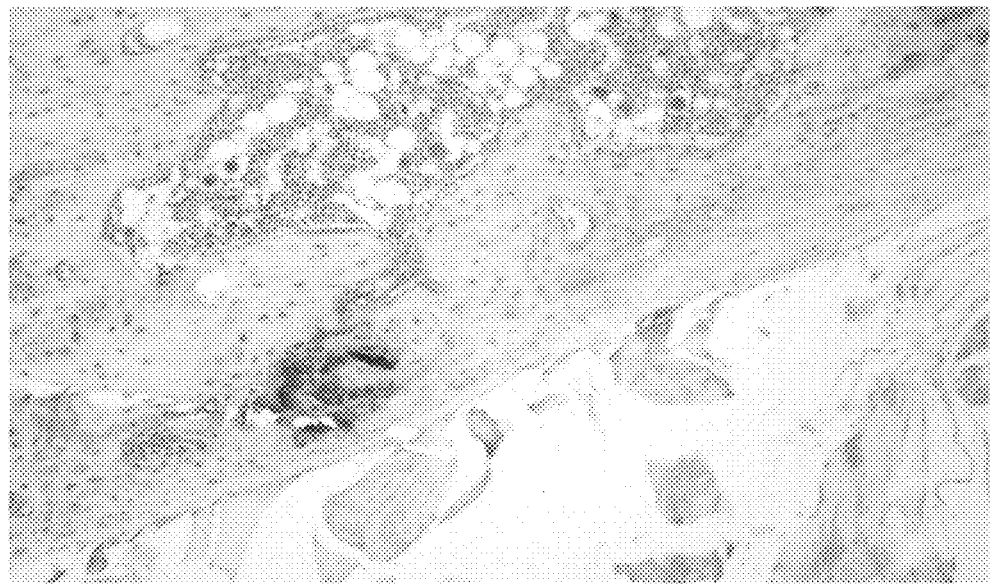
FIG. 12 shows the results obtained when mammospheres from CCCs-enriched cellular population are injected into the bone marrow of a SCID mouse. After two months (A) abnormal outgrowth of tumor is seen on the medial aspect of the tibia as seen by X-ray with bone disruption, (B) as seen with micro-CT scan results, (C) confirmed by Masson-Goldner staining as well as with an anti-CK8 antibody staining at magnification (D) 10× and (E) 40×. Cartilage disruption is also observed.
Figure 12E:
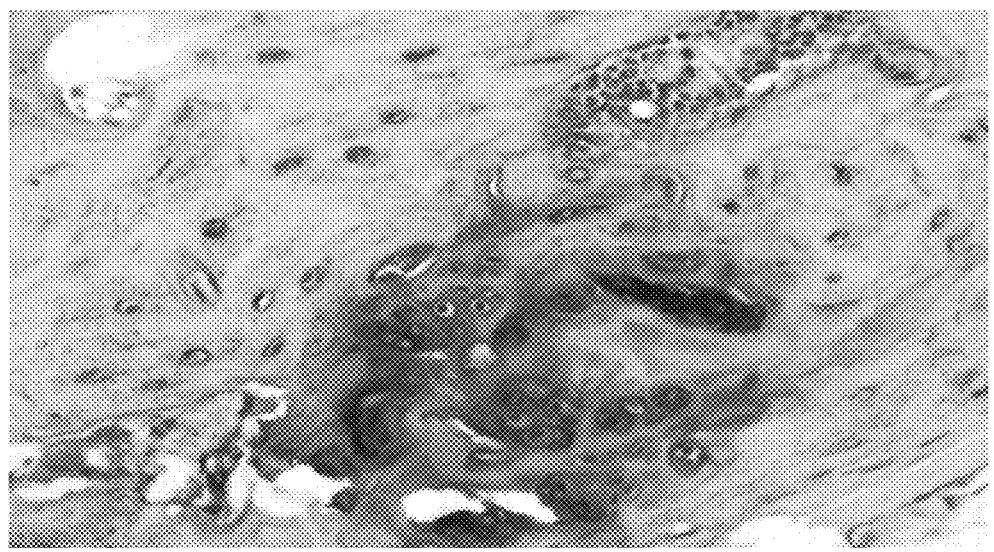

CCCs-enriched cellular populations were purified by Robosep® and grown in adherent 6-well plates in MammoCult™ medium. Medium was changed weekly. After 6 weeks in culture, cells were trypsinized and 30 000 cells were injected intra-tibially in 6-week old female NOD-SCID mice. Animal were sacrificed 8 weeks post-injection. Bone was fixed formalin and decalcified and embedded in paraffin. IHC staining done with anti-human CK8 antibody (progen, heidelberg Germany cat #GP11). When CCCs-enriched cellular populations were injected into the mouse tibia, after two months (FIG. 12A) abnormal outgrowth of tumor is seen on the medial aspect of the tibia seen by X-ray with bone disruption. FIG. 12B shows micro-CT scan results with the abnormal outgrowth. FIG. 12C confirms, by Masson-Goldner staining, abnormal growth and shows cartilage disruption. FIGS. 12D and 12E confirm the epithelial nature of the abnormal growth.

Example III

Drug-Sensitivity Assay

One or more frozen aliquot of RoboSep™ CD45-negative cell population (described in Example I and containing about $5 \times 10^6$ nucleated cells and about 1 000 to 3 000 CTCs based on Epimet™-positive staining) is cultured in the conditions described in Example II until approximately 600 000 cells are obtained (usually after 6 subculture steps). This amount of cells is sufficient for testing four distinct compounds in triplicate at four different concentrations using a plating density of approximately 5 000 to 10 000 cells/well in 96-well plates. Cells are plated onto ultra-low attachment microtiter plates at 5 000 to 10 000 cells/well in 125 µL of fresh MammoCult™ media in triplicates. Experimental and control samples (no cells added) are incubated for 24 hours at 37° C. and 5% $CO_2$. The MammoCult™ media is then replaced by 125 µL of the test compounds is diluted in MammoCult™ media at final concentrations of 0.01, 0.1, 10 and 100 µM. Incubation is prolonged for another 48 hours. Following incubation, 25 µL of AlamarBlue™ reagent (Invitrogen, Carlsbad, Calif.) is added directly to the cells in culture medium and incubated for an additional 3 hours. Fluorescence intensity (FI) is determined using a spectrofluorometer (excitation: 530-560 nm; emission: 590 nm). Dose response curves are calculated as a percentage of untreated controls ($FI_{590}$ of test agent dilution/$FI_{590}$ of untreated control)×100 and the $LD_{50}$ are calculated.

Figure 13:
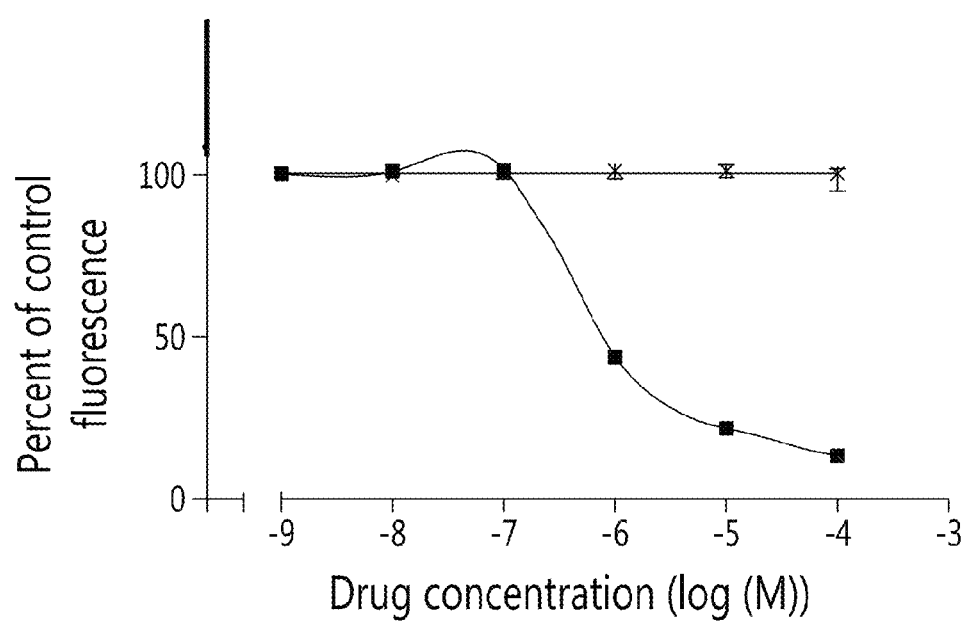
FIG. 13 shows the percent in fluorescence (when compared to a control) in function of the concentration (provided as log(M)) of cultured CCCs treated with Epirubicin (■) or Paclitaxel (♦).

Cells were collected by aphaeresis from a breast cancer patient (ER+, PR-, HER2 (2+)) diagnosed with invasive lobular carcinoma and metastatic spread to bone, liver and the mediastinum. This patient had become clinically resistant to taxol but was considered responsive to epirubicin. The CCC cells were obtained as explained in Example I and grown in the MammoCult™ media (Stem Cells Technology, Vancouver, BC). The cells were trypsinized to obtain single cells in suspension and plated into low attachment 96-well plate in duplicates at a concentration of 10 000 cells per well. Twenty-four hours later, increasing concentrations of either taxol (paclitaxel) or epirubicin were added and the cells incubated for another 48 hours. Cell growth/viability was assessed using Presto Blue®(Invitrogen). Upon entering a living cell, PrestoBlue® reagent is reduced from resazurin, a blue compound with no intrinsic fluorescent value, to resorufin which is red in color and highly fluorescent. Conversion is proportional to the number of metabolically active cells. Fluorescence values use the excitation and emission peaks for resorufin. Five hours following addition of the Prestoblue® dye, fluorescence was read and the percentage of fluorescence in cells treated with either taxol or epirubicin over fluorescence in vehicle-treated cells calculated. As shown on FIG. 13, epirubicin (the 4-epimer of doxorubicin) induces a dose dependent inhibition of cell growth with an $IC_{50}$ of around $10^{-6}$ M, whereas taxol had no effect on cell growth.

While the invention has been described in connection with specific embodiments thereof, it will be understood that the scope of the claims should not be limited by the preferred embodiments set forth in the examples, but should be given the broadest interpretation consistent with the description as a whole.

What is claimed is:

1. A method of providing a population of cells enriched in circulating cancer cells from a subject having a melanoma or a carcinoma, the method comprising:
   a) obtaining an apheresis nucleated cellular product from the subject containing at least about $10^9$ nucleated cells;
   b) removing CD45 positive leukocytes from the apheresis nucleated cellular product to provide the population of cells enriched in circulating cancer cells;
   c) collecting the population of cells enriched in circulating cancer; and
   d) culturing the population of cells enriched in circulating cancer cells.

2. The method of claim 1, wherein step d) further comprises culturing the population of cells enriched in circulating cancer cells in non-adherent conditions.

3. The method of claim 2, wherein step d) further comprises culturing the population of cells enriched in circulating cancer cells in conditions allowing the formation of at least one mammosphere.

4. The method of claim 3, wherein the at least one mammosphere comprises circulating stem cells and step d) further comprises collecting the at least one mammosphere to obtain a population enriched in circulating stem cells.

5. The method of claim 1, further comprising, prior to step c), selecting cytokeratin (CK)-positive cells from the population of cells enriched in circulating cancer cells.

6. The method of claim 5, wherein the population of cells enriched in circulating cancer cells is a population of cells enriched in circulating tumor cells and step c) further comprises collecting the population of cells enriched in circulating tumor cells.

7. The method of claim 1, further comprising, prior to step c) selecting epithelial cellular adhesion molecule (EpCAM)-positive-positive cells from the population of cells enriched in circulating cancer cells to obtain a population of cells enriched in circulating tumor cells and step c) further comprises collecting the population of cells enriched in circulating tumor cells.

8. The method of claim 1, further comprising, prior to step c), selecting CD24-negative and CD44-positive cells from the population of cells enriched in circulating cancer cells to provide a population of cells enriched in circulating stem cells, and, at step c), collecting the population of cells enriched in circulating stem cells.

9. The method of claim 8, further comprising, prior to step c) selecting aldehyde dehydrogenase isoform 1 (ALDH1)-positive cells and/or EpCAM-negative cells from the population of cells enriched in circulating cancer cells to provide the population of cells enriched in circulating stem cells.

10. The method of claim 1, further comprising, prior to step c), selecting CK-negative cells from the population of cells enriched in circulating cancer cells to obtain a population of cells enriched in circulating epithelial mesenchymal transition cells and, at step c), collecting the population of cells enriched in circulating epithelial mesenchymal transition cells.

11. The method of claim 10, further comprising, prior to step c), selecting vimentin-positive cells, E-cadherin-negative and/or N-cadherin-positive cells from the population of cells enriched in circulating cancer cells to obtain the population of cells enriched in circulating epithelial mesenchymal transition cells.

12. The method of claim 1, wherein the carcinoma is a breast carcinoma, a colorectal carcinoma, a prostate carcinoma or a lung carcinoma.

13. The method of claim 1, wherein the subject is a human.

* * * * *